US011238968B1

(12) United States Patent
Farr et al.

(10) Patent No.: US 11,238,968 B1
(45) Date of Patent: Feb. 1, 2022

(54) AUDITABLE ASSET TRACKING MODEL

(71) Applicant: Atadas, Inc., Salt Lake City, UT (US)

(72) Inventors: William Farr, Kamas, UT (US); Scot Joseph Penrod, Pleasant View, UT (US)

(73) Assignee: ATADAS, INC., Salt Lake City, UT (US)

( * ) Notice: Subject to any disclaimer, the term of this patent is extended or adjusted under 35 U.S.C. 154(b) by 0 days.

(21) Appl. No.: 17/375,275

(22) Filed: Jul. 14, 2021

Related U.S. Application Data

(60) Provisional application No. 63/147,664, filed on Feb. 9, 2021.

(51) Int. Cl.
| | | |
|---|---|---|
| *G06Q 10/00* | (2012.01) | |
| *G06K 9/00* | (2006.01) | |
| *G16H 20/10* | (2018.01) | |
| *G16H 70/40* | (2018.01) | |
| *G16H 40/20* | (2018.01) | |
| *G16H 15/00* | (2018.01) | |
| *G06F 21/60* | (2013.01) | |
| *H04L 29/06* | (2006.01) | |
| *H04W 4/14* | (2009.01) | |
| *G06T 7/10* | (2017.01) | |
| *G06F 3/0482* | (2013.01) | |

(Continued)

(52) U.S. Cl.
CPC .......... *G16H 20/10* (2018.01); *G06F 3/0482* (2013.01); *G06F 21/602* (2013.01); *G06T 7/10* (2017.01); *G16H 15/00* (2018.01); *G16H 40/20* (2018.01); *G16H 70/40* (2018.01); *H04L 63/164* (2013.01); *H04W 4/14* (2013.01); *G06F 2221/2107* (2013.01); *G06T 2207/20081* (2013.01); *G16H 10/60* (2018.01); *G16H 40/67* (2018.01)

(58) Field of Classification Search
USPC ....... 382/100, 103, 108, 112, 115, 123, 128, 382/143, 156, 162, 168, 180–189, 199, 382/209, 219, 232, 254, 276, 286–294, 382/305, 312; 705/2, 3; 700/244
See application file for complete search history.

(56) References Cited

U.S. PATENT DOCUMENTS

| | | | | |
|---|---|---|---|---|
| 2007/0016443 A1* | 1/2007 | Wachman | .............. | G16H 70/40 705/2 |
| 2013/0197693 A1* | 8/2013 | Kamen | .................. | G16H 20/17 700/244 |

(Continued)

*Primary Examiner* — Seyed H Azarian
(74) *Attorney, Agent, or Firm* — Workman Nydegger

(57) ABSTRACT

A system can provide efficiency in monitoring prescription medication can include a client computer system configured to service a user interface (UI) for facilitating a pill counting procedure. The client receives a notification from a server computer system to initiate a pill count. The instructions can also cause the system to display a UI on the client computer system to facilitate the pill counting procedure. The displayed layout includes: (i) a timestamp field; (ii) a pill count field; (iii) an image field displaying an image of the pills the user has; (iv) a certification field; and (v) a submit field. On submission, the system can generate an encrypted data file comprising a secret key that de-identifies the user, the image of the pills, and metadata describing conditions associated with the pill count. The system can then transmit the encrypted data file to the server computer system.

20 Claims, 21 Drawing Sheets

(51) Int. Cl.
*G16H 40/67* (2018.01)
*G16H 10/60* (2018.01)

(56) References Cited

U.S. PATENT DOCUMENTS

2017/0199983 A1\* 7/2017 Cano .................. G07F 9/023
2017/0300659 A1\* 10/2017 Ziv .................. A61J 7/0076
2020/0152313 A1\* 5/2020 Hanina .............. G06K 9/00758
2020/0335192 A1\* 10/2020 Tupler .................. G16H 20/13

\* cited by examiner

Provider Properties
900

Provider Properties

| Data Properties | |
|---|---|
| Authorized Medical Director: | Yes |
| DEA Waiver Limit: | 275 |
| Provider Name: | Dr. Peter Farr MD |
| Your NPI: | 123 |
| Your X DEA Number: | X456 |
| Address 1: | 10967 Allisonville Rd |
| Address 2: | Suite 110 |
| City: | Fishers |
| State: | IN |
| Zip: | 46038 |
| Phone: | 317-559-7970 |
| Email: | pfarr@beaconpc.com |

*FIG. 9*

Pill Count UI
1900

AUDITABLE ASSET TRACKING MODEL

CROSS-REFERENCE TO RELATED APPLICATIONS

This application claims the benefit of and priority to U.S. Provisional Patent Application Ser. No. 63/147,664 filed on Feb. 9, 2021 and entitled "AUDITABLE ASSET TRACKING MODEL," which application is expressly incorporated herein by reference in its entirety.

BACKGROUND

An "opioid" is a type of pain-relieving drug that interacts with the opioid receptors in a person's cells. Opioids can be made from plants and can also be synthesized in a laboratory. To work, the drug travels through a person's cardiovascular system and attaches to the opioid receptors in a person's brain cells. As a result of this attachment, the cells release signals that effectively stifle the ability to feel pain.

The year 2020 was the worst year for opioid overdose in the United States. For example, there were over 80,000 deaths in 2020 with opioids as the majority contributor to overdoses. Each year, there are about 90 million people on pain medication. Due to the ease by which addiction occurs, opioid prescriptions as a controlled substance are heavily regulated by the DEA (Drug Enforcement Agency). Consequently, the DEA works extensively with medical professionals to manage controlled substance distributions.

Currently, there are between 2-3 million people in the United States who have OUD (Opioid Use Disorder). FDA approved medications for OUD are correlated with positive outcomes for patients and society. The provision of these FDA approved medications by certified healthcare providers is referred to as Medication Assisted Treatment (MAT). MAT has proven to reduce overdose deaths related to OUD. Unfortunately, only a small percentage of those people are actually being treated through a MAT. In an effort to help people experiencing OUD, the DEA allows medical professionals to treat these patients with approved FDA medications. That being said, there is still a need for oversight to prevent against "diversion control," which occurs when a patient sells his/her pills on a black market.

Currently, the DEA allows a medical professional to have only up to 275 MAT patients. In order to treat people experiencing OUD, a medical professional is required to obtain a waiver to provide MAT. Federal regulations were implemented per the Drug Addiction Treatment Act of 2000 (DATA 2000), which allows qualifying healthcare providers to obtain a federal waiver to prescribe Schedule III and V opioids (FDA-approved) for OUD treatment in an office-based opioid treatment (OBOT) setting. The DEA will grant the medical professional a waiver or permission so the medical professional can manage those MAT patients. Such waivers or programs are controlled, not only in the number of patients enrolled but also in record keeping, auditing, and other factors. For example, one requirement imposed on medical professionals who provide MAT services is that of requiring their patients to perform a routine or periodic pill count procedure in support of the DEA Diversion Control Division mission to prevent and detect suspicious activity related to the diversion or dispersion of controlled pharmaceuticals (substances) from legitimate sources. Moreover, the US Food and Drug Administration (FDA) only has a finite number of medications approved to prescribe specifically for OUD MAT.

Generally, a pill count procedure involves the medical professional meeting with the patient and the two of them verifying how many pills the patient has at any given time. For example, FIG. 1 shows an example of a patient 100 who has been prescribed a number of pills 105. The patient 100 and medical professional pair may be tasked with counting the pills.

By counting the number of pills, the medical professional can gauge whether illicit activity is occurring with the pills (e.g., overdosing, underdosing, or perhaps selling the pills). Traditionally, the pill counting process involved the medical professional either meeting the patient in-person or meeting the patient over a video call. Time was then used for the medical professional and the patient to review and count the pills. The medical professional would then have to generate records, which may be subject to an audit by the DEA. Such pill counting techniques expend a significant amount of the medical professional's time, thereby diverting the professional from other activities he/she could be engaged in. Accordingly, there are a number of disadvantages in the fields related to medical monitoring of end usage items that can be addressed.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY OF THE INVENTION

Implementations of the present invention include systems, methods, and computer program products that provide efficiency in the medical relationship, with particular regard to monitoring of end usage items, such as prescription medication.

For example, in some implementations, a client computer system configured to surface a user interface (UI) that facilitates a pill counting procedure can include one or more processors, and one or more computer-readable hardware storage devices that store instructions that are executable by the one or more processors. Upon execution, the instructions can cause the client computer system to at least receive a notification from a server computer system, where the notification includes information instructing that the pill counting procedure is to be performed. The system also surfaces (e.g., in response to the notification) the UI to a user of the client computer system, where the UI has a particular visual layout designed to facilitate the pill counting procedure. Optionally, the particular visual layout includes: (i) a timestamp field indicating a date and time when the pill counting procedure is performed; (ii) a pill count field indicating how many pills the user has remaining at that time; (iii) an image field displaying an image of the pills the user has; (iv) a certification field that, when selected, operates as a certification on a part of the user that the pill count is accurate; and (v) a submit field/button. The system can further be configured so that, in response to the submit field being selected, the system generates an encrypted data file comprising a secret key that de-identifies the user, a site code that identifies a database of a medical professional, the image of the pills, and metadata describing conditions associated with the pill count. The system can then transmit the encrypted data file to the server computer system.

In some embodiments, a server computer system is configured to facilitate a pill counting procedure. For instance, in response to a scheduled pill counting reminder being triggered, the server can transmit a notification to a client computer system. The notification includes information instructing a user of the client computer system to initiate a pill counting event. The server receives (e.g., from the client computer system) an encrypted data file comprising a secret key that de-identifies the user of the client computer system, a side code that identifies a database of a medical professional, an image of pills the user has, and metadata describing conditions associated with the pill counting event. The server then decrypts the encrypted data file to extract the secret key, the image, and the metadata. Based on the secret key, the server identifies the user within a database managed by the server computer system. The server also generates a new log record for the user within the database, where the new log record comprises the image and the metadata. Additionally, the server generates a report detailing the new log record.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be obvious from the description, or may be learned by the practice of the teachings herein. Features and advantages of the invention may be realized and obtained by means of the instruments and combinations particularly pointed out in the appended claims. Features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features can be obtained, a more particular description of the subject matter briefly described above will be rendered by reference to specific embodiments which are illustrated in the appended drawings. Understanding that these drawings depict only typical embodiments and are not therefore to be considered to be limiting in scope, embodiments will be described and explained with additional specificity and detail through the use of the accompanying drawings in which:

FIG. 9 illustrates an example UI structured to track properties of a health care provider.

DETAILED DESCRIPTION

Figure 1:
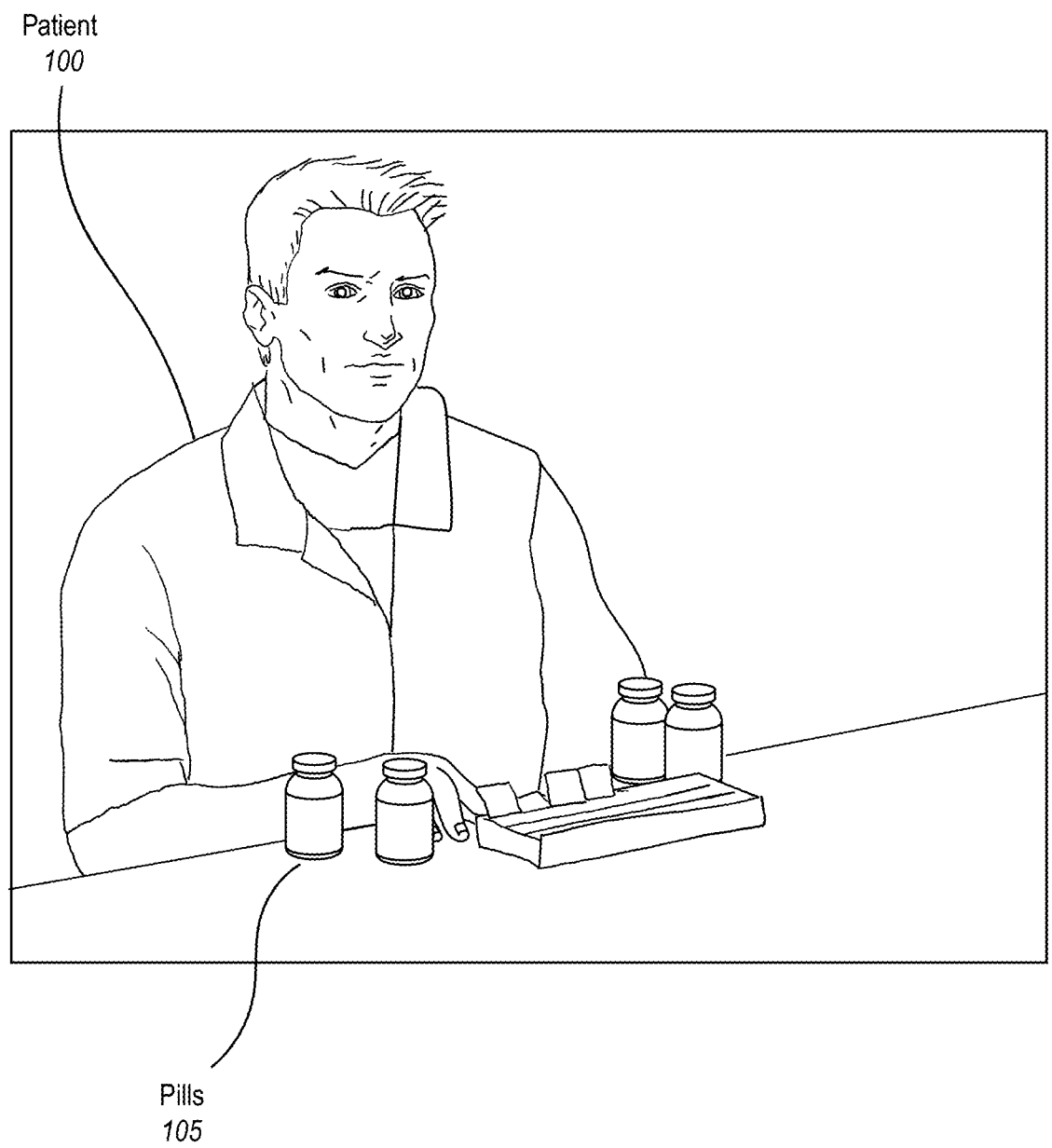
FIG. 1 illustrates a scenario where a patient is counting his pills.

Embodiments disclosed herein relate to systems, devices, and methods that facilitate an improved pill counting procedure.

In some embodiments, a client computer system is provided with an application that is used to facilitate the pill counting procedure. The application receives a notification from a server computer system, where the notification triggers the user to initiate the pill counting procedure. The application displays a user interface (UI) having a particular visual layout designed to improve how the user interacts with the system. The UI prompts the user to enter certain information related to the pill counting event. The UI also prompts the user to use a camera to generate an electronic image of the user's pills. The UI is further structured to prompt the user to certify the accuracy and authenticity of the pill count event. Once the certification has been performed, the application then generates a data file comprising a secret key, which de-identifies the user's identity to prevent illicit systems from learning of the user's identity (e.g., in the event the data file is intercepted) but which enables the server computer system to recognize the user. The data file also includes the image and additional metadata describing parameters associated with the pill count event. The data file is encrypted and then transmitted to the server computer system.

In some embodiments, the server computer system triggers the transmission of the notification to the client computer system. This notification is sent via an SMS text message transmitted over a telecommunications network. The server computer system is also configured to receive the encrypted data file from the client computer system. Notably, although the notification from the server to the client was transmitted over a telecommunications network, the encrypted data file is transmitted over a different network, such as via the Internet using the IP protocol. The server computer system decrypts the encrypted data file, parses the information, and generates a new record for the specific patient, who is identified using the secret key. Optionally, machine learning (ML) may be executed against the image to perform object segmentation to identify the pills (e.g., to determine a type for each pill represented within the image) and to count the pills as an additional verification technique.

Examples of Technical Benefits, Improvements, and Practical Applications

The following section outlines some example improvements and practical applications provided by the disclosed embodiments. It will be appreciated, however, that these are just examples only and that the embodiments are not limited to only these improvements.

The disclosed embodiments bring about substantial, material, and practical improvements to the support of federal regulations governing the pill counting field. As described earlier, traditional systems were laborious and consumed a substantial amount of time on the medical professional's part. The disclosed embodiments, on the other hand, significantly speed up the process, thereby enabling the medical professional to focus his/her efforts on other matters.

The embodiments also provide a unique UI designed to help users better interact with the computer system. As described earlier, it is often the case that patients may have an addiction to opioids. The specific visual layout of the disclosed user interface helps patients calmly and efficiently navigate the various screens, thereby improving the user's experience. The server-side UIs also help medical professionals quickly navigate the various fields to certify or validate the pill count metrics.

The embodiments provide additional benefits to the technical field through the use of specially trained machine learning (ML) algorithms. Such algorithms are trained not only to recognize and differentiate pills but also to provide an accurate verification regarding the pill count. Using the disclosed ML algorithms helps medical professionals in a substantial way by automating the counting process using an intelligent algorithm.

The embodiments also improve the art by providing a broad array of mitigation operations that may be performed in the event of suspicious activity. These mitigation operations can help reduce the stress levels of patients (e.g., by simply requiring an additional pill count as opposed to worrying the patient with enhanced probing questions or queries). Additionally, these mitigation operations help medical professionals better manage situations involving suspicious activity. Accordingly, the disclosed embodiments bring about numerous beneficial and practical applications to the technical field. These and other benefits will be described in more detail throughout the remaining portion of this disclosure.

Example Architecture for Facilitating Pill Counting

Figure 2:
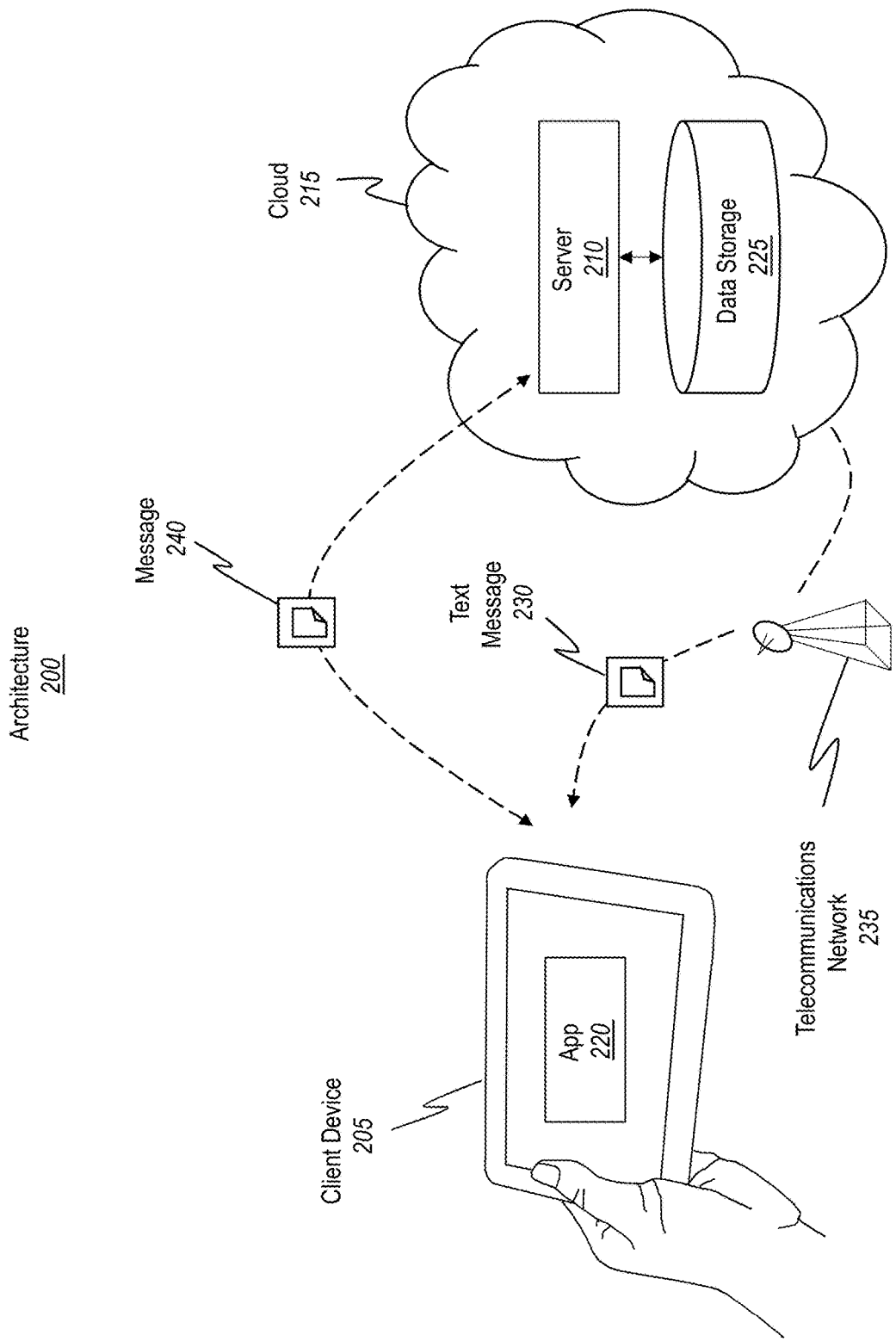
FIG. 2 illustrates an example architecture structured to facilitate a pill counting procedure.

Having just described a few of the benefits provided by the disclosed embodiments, attention will now be directed to FIG. 2, which illustrates an example architecture 200 designed to facilitate the improved processes for pill counting. The discussion surrounding architecture 200 is provided as an initial high-level overview of some of the operations performed by the disclosed embodiments. Further details regarding specific operations will be provided later in subsequent figures.

As shown, architecture 200 includes a client device 205. Client device 205 may be any type of device, including portable devices, stationary devices, mobile devices, handheld devices, wearable devices, smart phones, and so forth, without limit.

Architecture 200 also includes a server 210 operating in a cloud 215 environment. Server 210 may be any type of server computing device, without limit.

The client device 205 is shown as executing a client-side application or "app" 220. As will be discussed in more detail later, app 220 is designed to surface a user interface (UI) structured to improve how the user interacts with the client device 205 in order to perform pill counting. Further details on this app 220 will be provided later.

The server 210 is shown as managing and/or communicating with a data repository, as shown by data storage 225. The data storage 225 includes a database that manages or maintains patient information, such as prescriptions, dosage amounts, pill counts, and other information.

In accordance with the disclosed principles, the embodiments provide full isolation between medical professional records and between patient records. That is, instead of using a multi-tenancy platform, the embodiments instantiate a new instance of a database for each medical professional. Using new instances for each medical professional prevents cross contamination or leakage between data sets. In some cases, the database is encrypted. Different types of databases may be used, such as Microsoft SQL Server, My SQL, Oracle, and so on.

The provider database has a unique "site" code for that provider or medical professional. The provider is able to enter provider, patient, and prescription data into the database. Additionally, the system is able to generate an activation code per patient and an internal secret key per patient relative to that medical professional's database. Such information may be used to initiate a patient record and to update that record when new data is made available. Further details on that information will be provided later.

With the architecture 200, the server 210 is able to trigger the sending of a text message 230 via a telecommunications network 235. That is, when a scheduled pill counting event occurs, the server 210 is able to trigger the sending of the text message 230 to the client device 205. The text message 230 can operate as a notification to the user of the client device 205. The notification informs the user that he/she should initiate the pill counting procedure on the client-side. As will be described in more detail later, medical professionals are provided with high levels of customizability and can schedule when pill counting events are to occur.

Other notification techniques may also be used instead of a text message (e.g., an SMS message). Indeed, emails, phone calls, or any other notification technique may be used.

When the client device 205 receives the notification (e.g., the text message 230), the notification operates as a trigger informing the user that he/she should use the app 220 to begin the pill counting procedure. The results of the pill counting procedure (to be discussed later) are then transmitted back to the server 210 in the form of the message 240. This message 240 may include a picture of the pills, a secret key used to de-identify the user, and other metadata describing the pill counting event/procedure. Further details on that message 240 will be provided later.

In any event, the message 240 is transmitted from the client device 205 to the server 210. In some implementations, the message 240 (e.g., perhaps an encrypted data file) is directed to a URL with a related medical professional's database site code associated with the server 210, and an API intercepts the message 240, parses the message 240, and then generates a new record in the data storage 225. In this regard, the message 240 can be directed to a URL associated with a server computer system, and an API can be configured to intercept the message 240.

Therefore, in such instances, the message 240 may be transmitted using the IP protocol. In some implementations, other protocols or transmission techniques may be used, such as text messages over a telecommunications network. Accordingly, different transmission techniques may be utilized to provide the results of the pill counting procedure to the server 210.

With this architecture 200, patients and medical personnel are able to collaborate and communicate with one another. Additionally, this architecture 200 provides a robust platform for counting pills and for providing an auditable asset (e.g., pill) management process.

Figure 3:
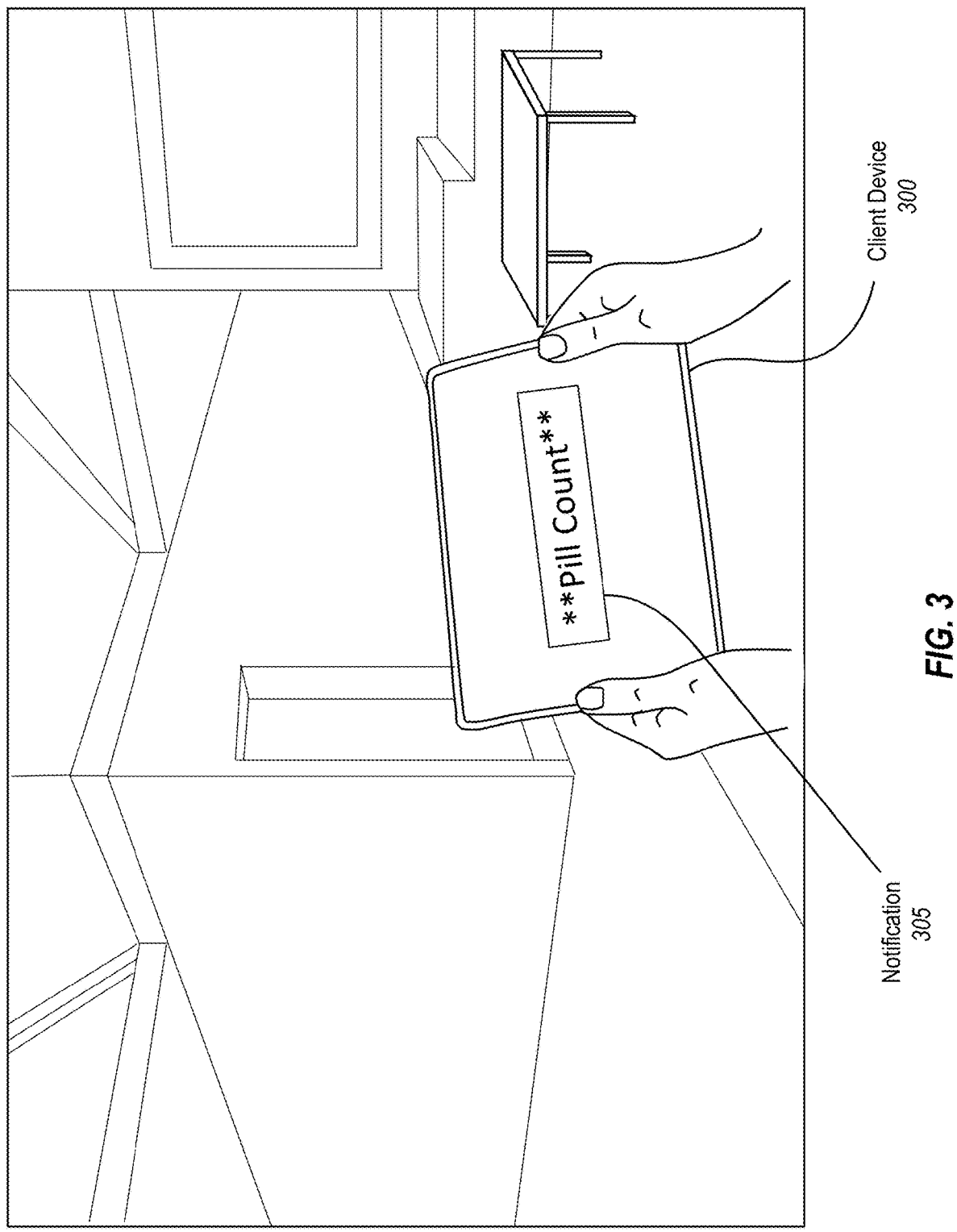
FIG. 3 illustrates how a reminder can be displayed on a client device in order to prompt the user of the client device to count his/her pills.

FIG. 3 shows a client device 300, which is representative of the client device 205 of FIG. 2. FIG. 3 also shows an initial notification 305, which is operating as an alert to inform the user of the client device 300 that he/she should count pills. The notification 305 is an example of the text message 230.

Figure 4:
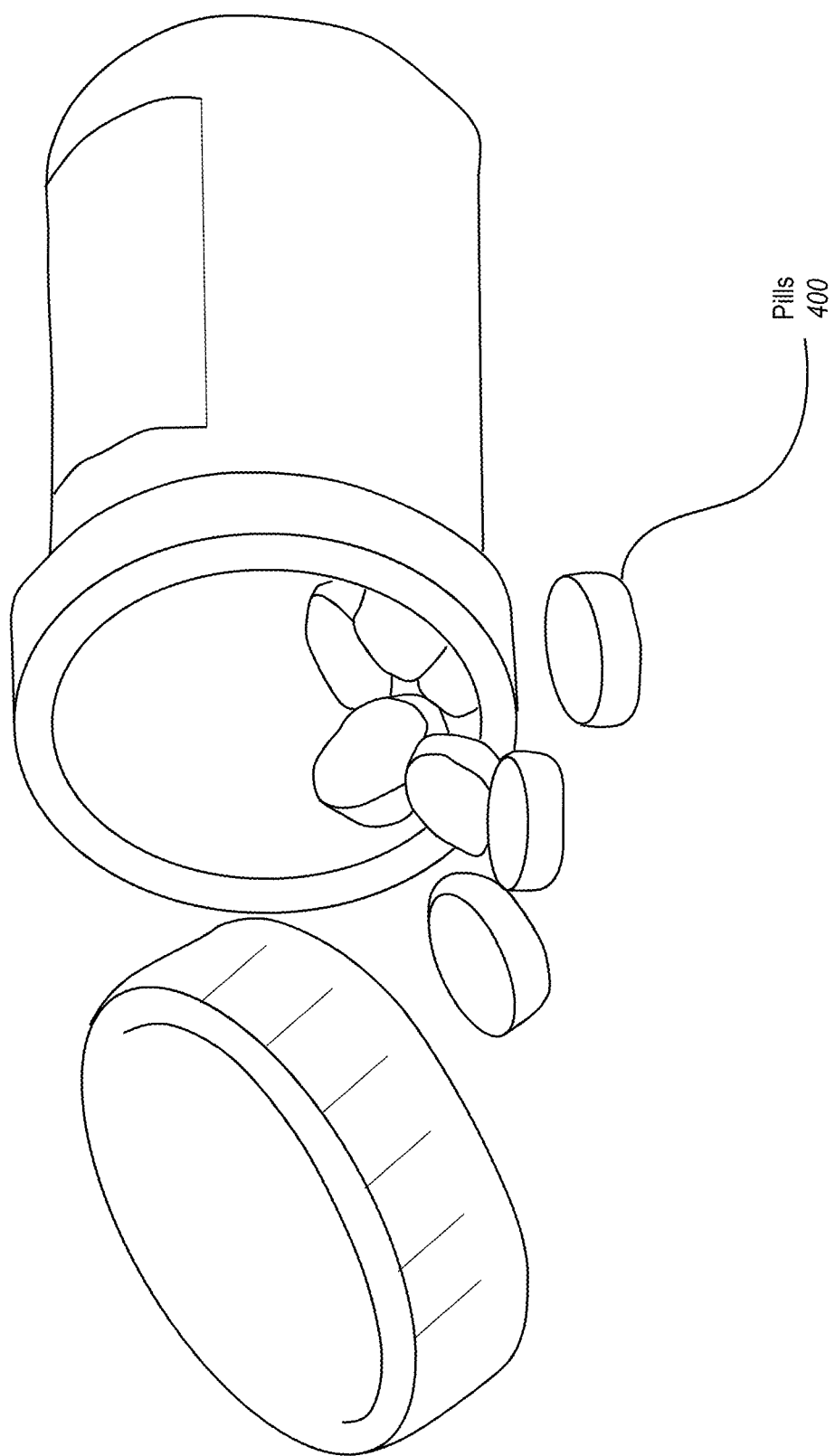
FIG. 4 illustrates pills that are to be counted.

In response to receiving the notification 305, the user will then search for and gather his/her controlled substance pills, as shown by the pills 400 of FIG. 4. It may be the case that the user/patient has multiple different controlled substances. Consequently, the user will be tasked with gathering those pills so he/she can count them. In some cases, the notification received from the server computer system is received via a SMS text message.

Figure 5:
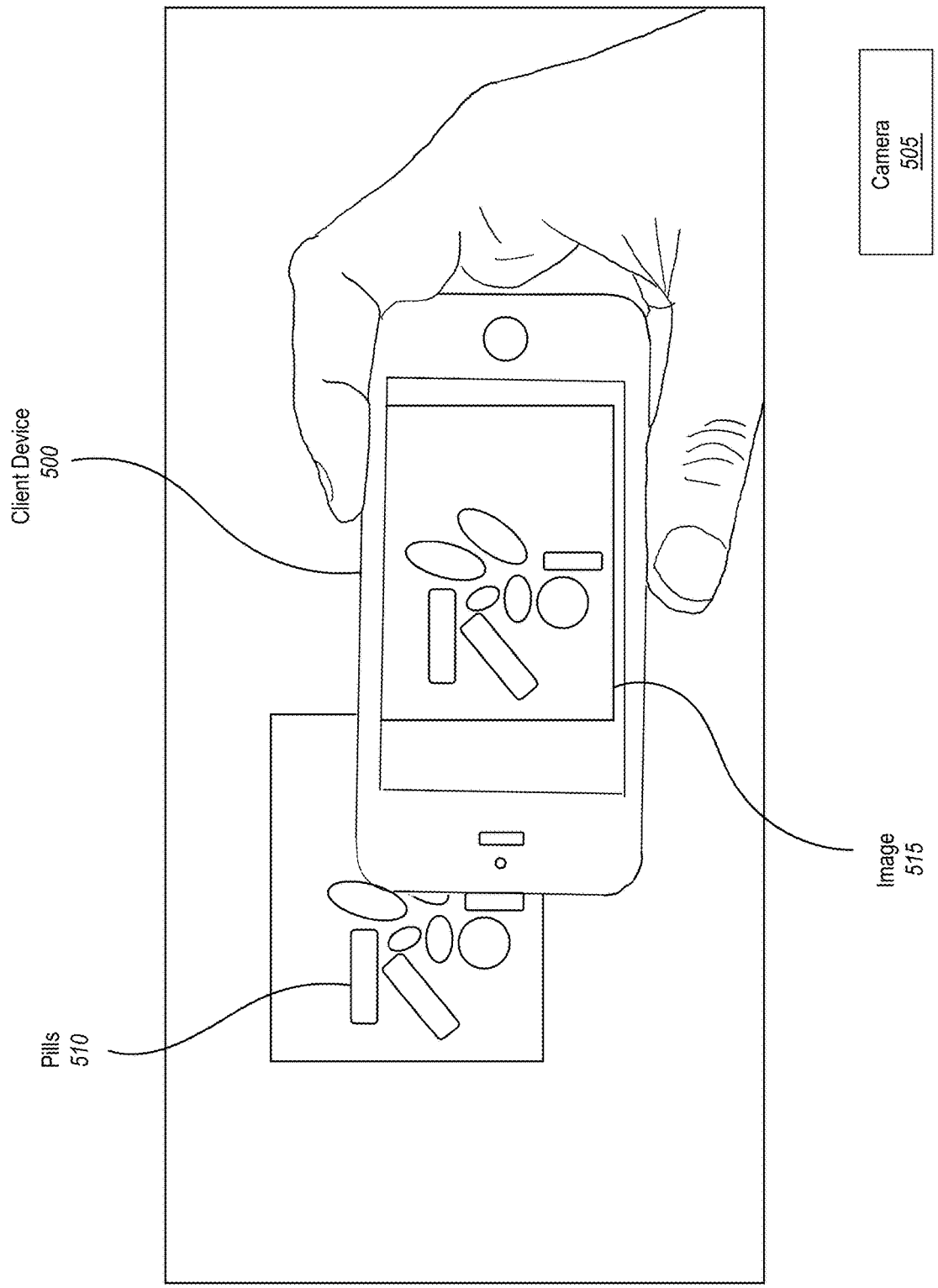
FIG. 5 illustrates a scenario in which the user is using his client device, which includes a camera, to take a picture of the pills.

FIG. 5 shows one example process for counting pills. In particular, FIG. 5 shows a client device 500, which is representative of the client devices mentioned thus far. This client device 500 includes one or more cameras, as shown by camera 505. The user is able to use the camera 505 to generate an image of his pills 510, as shown by the image 515. This image 515 operates as a trackable digital record detailing how many pills the user currently has in his possession. This image 515 will be provided to the server mentioned earlier, as shown in FIG. 6. In some cases, the image of the pills is embedded with the date and time when the pill counting procedure was performed.

Figure 6:
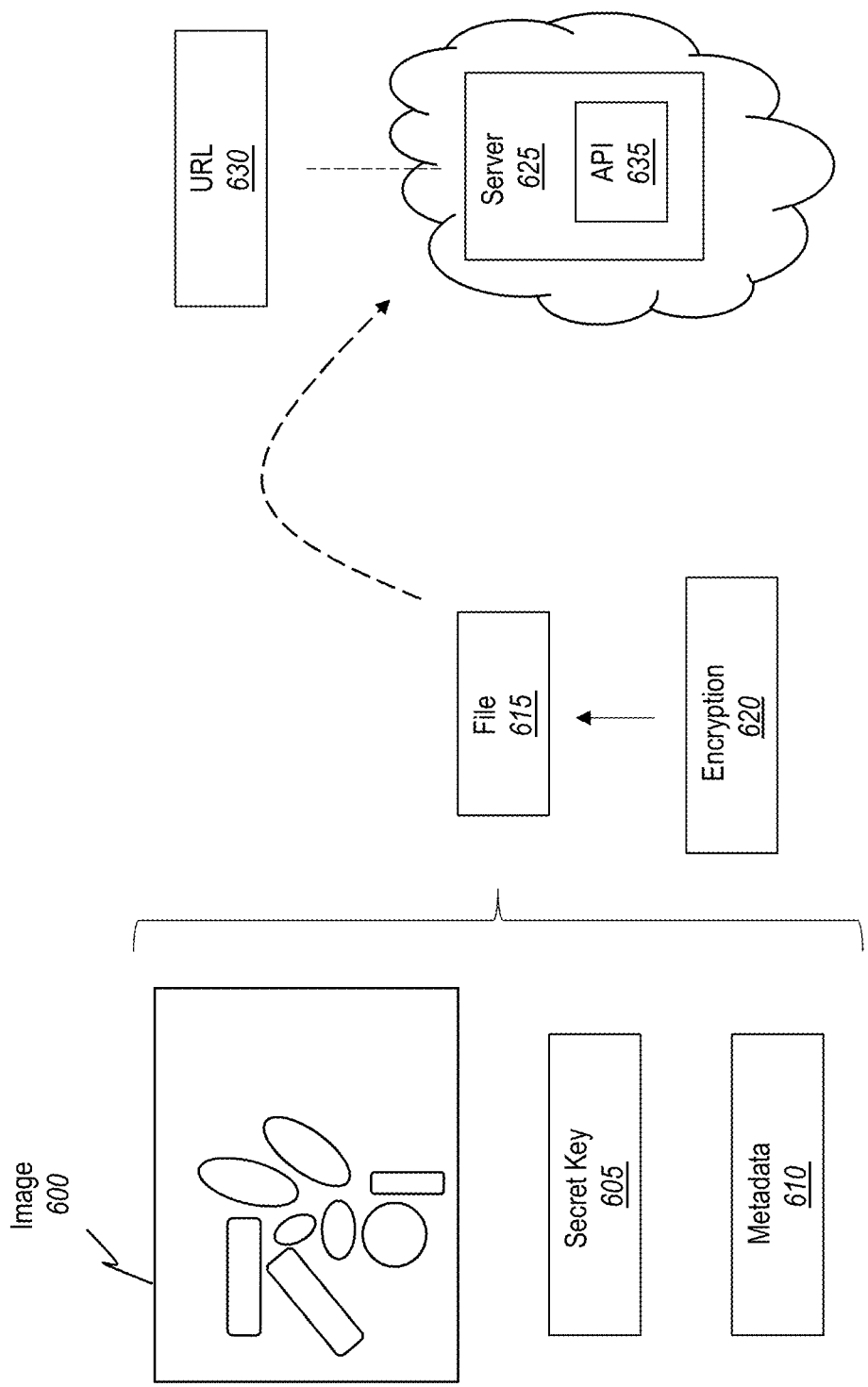
FIG. 6 illustrates the generation and transmission of a unique data file, which is structured to include an image, a secret key, and metadata associated with the pill count.

FIG. 6 shows an image 600, which is representative of the image 515 from FIG. 5. In accordance with the disclosed principles, it is desirable to maintain the user's confidentiality. Indeed, various government regulations mandate that patient information should not be inadvertently disclosed. As a result, the embodiments utilize a so-called secret key 605, which is designed to "de-identify" the user in the event that the user's data is intercepted when being transmitted from the client device to the server.

The secret key 605 may be any combination of numbers, letters, symbols, and so forth. In some cases, the secret key 605 may be a hash number that is generated based on user information, such as perhaps information extracted from the user's client device (e.g., IP address, MAC address, SIM card code, etc.), information about the user (e.g., name, birth date, social security number, phone number, address, etc.), and so on. That is, this information may be used to generate a hash number that is used to de-identify the user.

In some cases, on the server side, the server (e.g., server 210 from FIG. 2) is able to derive the secret key 605 in order to also identify the user. That is, the server may include the same information mentioned above and can use that information to generate the secret key 605. When the server receives the secret key 605, the server can use its existing information to derive secret keys. Whichever patient's information is successfully used to generate the secret key 605 will then inform the server which patient sent the image 600.

Below is an example of an activation code, secret key, and a site code. In some cases, the activation code and the secret key uniquely define a particular patient record communicated between the server database and the mobile application, while the site code uniquely defines the destination medical professional's database. Messages or records containing these pieces of information may be encrypted and later decrypted when the various transactions are processed.

ActivationCode=925ca271981
SecretKey=b0aac0bffd2376d1895af6e26fd651
SiteCode=pfarmd Metadata 610 is also collected. Metadata 610 describes circumstances, parameters, or characteristics surrounding the pill counting event. Examples of metadata 610 include, but certainly are not limited to, information about the client device (e.g., make, model, phone number, etc.), information as to when the user started the pill counting process (e.g., date, time, etc.), information as to how long it took the user to complete the pill counting process, and even location information (e.g., GPS coordinates). The metadata 610 may also include a number provided by the patient, where the number indicates the number of pills counted by the patient.

Other metadata information may include a picture of the user who is performing the pill counting process (e.g., the camera can also be used to capture an image of the user). Capturing an image of the user can help mitigate detecting suspicious activity related to the diversion of controlled pharmaceuticals (substances) from legitimate sources on the part of the user. In some cases, the application is designed to simultaneously use both a front-facing camera and a back-facing camera. For instance, the front-facing camera can record the face of the user while the back-facing camera can record the pills. These images, or perhaps even a video stream, can be generated simultaneously with one another and then perhaps stitched together to form a single image (e.g., with one image being on the left hand side and the other image being on the right hand side, or vertical alignment or any other alignment). In some cases, the images can be thumbnail images that have been stitched together. In some cases, a timestamp is added to the image(s) themselves and perhaps flattened so as to become an integrated part of the image(s).

That is, various images can be included as parts of a composite image. For instance, a first image can be generated by a back-facing camera of the client computer system, where the first image is of the pills. A front-facing camera of the client computer system can generate a second image of the user while the back-facing camera generates the first image. The composite image is then generated and includes both the first image and the second image such that a likeness of both the user and the pills are displayed in the same composite image.

Stated differently, the image can be included as a part of a composite image that is at least partially generated by a back-facing camera of the client computer system. A front-facing camera of the client computer system generates a second image of the user while the back-facing camera generates the image. The composite image includes both the image and the second image. As a consequence, a likeness of both the user and the pills are displayed in the same composite image.

Additional information includes the user's fingerprint, which can be obtained via a touchscreen of the client device. As such, the metadata can include a fingerprint of the user and/or any other biometric data of the user. Additional information includes how long it took the user between the time when the initial reminder or alert was received and/or acknowledged and the time when the user actually started to count the pills.

A prolonged period of time between when the alert was received and when the pill counting process began may indicate suspicious activity on the part of the user. For example, prolonged periods of time may indicate that the user is gathering pills from other sources in an attempt to falsify his actual pill count. Therefore, including this information in the metadata 610 may be beneficial to identify suspicious activity. That is, the metadata can include a time counter reflecting an amount of time that elapsed from a time when the notification or text message was received to a time when a response was provided (e.g., an encrypted data file was sent to a server computer system).

In some instances, the metadata 610 may include a text or voice message from the user indicating why a delay in counting occurred or indicating some other potentially relevant information associated with the process. In some instances, the metadata 610 includes a voice recording that operates as verification the user is who he/she is asserting to be. That is, the metadata can include a voice recording of the user, where the voice recording operates as verification of the user's identity. Accordingly, the metadata 610 may include a wealth of information pertaining to the pill counting event.

In some cases, the metadata 610 includes location information, such as GPS information. The location information can also be used to help identify suspicious activity. For example, if the patient is a U.S. citizen, but the location data indicates the patient is currently in Madagascar, then that location may (potentially, though not necessarily) reflect some other entity has hacked the user's account. In this regard, the metadata can include GPS location data indicating a location where the image was generated or where the client computer system is located. The embodiments are able to detect whether a user is hiding his/her location via a VPN (virtual private network). If so, then the embodiments can instruct the user to temporarily turn off the VPN.

In accordance with the disclosed principles, the embodiments wrap or contain the image 600, the secret key 605, and the metadata 610 in a data file 615. This file 615 is then encrypted, as shown by encryption 620. Any number of encryption techniques may be used. In some embodiments, a SHA-1 (e.g., "Secure Hash Algorithm 1") cryptographic hash function is used to encrypt the file 615. The encrypted data file is eventually transmitted to the server computer system. In some cases, the encrypted data file is performed using the IP protocol.

In some cases, the image 600 is individually encrypted, the secret key 605 is individually encrypted, and the metadata 610 is individually encrypted. These encrypted pieces of information are then included in the data file 615. The file 615 may then be encrypted, thereby providing two layers of encryption.

In some cases, the image 600, the secret key 605, and the metadata 610 are included in the file 615 in an unencrypted form, and then the file 615 as a whole is encrypted. In any event, different encryption methods may be used, including but not limited to, symmetric encryption methods, asymmetric encryption methods, and hashing.

The client device prepares the file 615 and then transmits the file 615 to the server 625, which is representative of the servers discussed thus far. In some cases, the server 625 is associated with a URL 630, and the file 615 is directed to that URL 630 with a related medical professional's database site code.

The server 625 includes or is associated with an API 635. The API 635 receives or intercepts the file 615 directed to the URL 630. The API 635 decrypts the file 615, parses the image 600, the secret key 605, and the metadata 610 from the file 615, and then generates a new record for the user/patient associated with that file 615. Recall, each medical professional has his/her own instance of the database, which is identified by a unique site code and which is used to track and monitor information. As such, a new record is generated within that professional's database instance.

Figure 7:
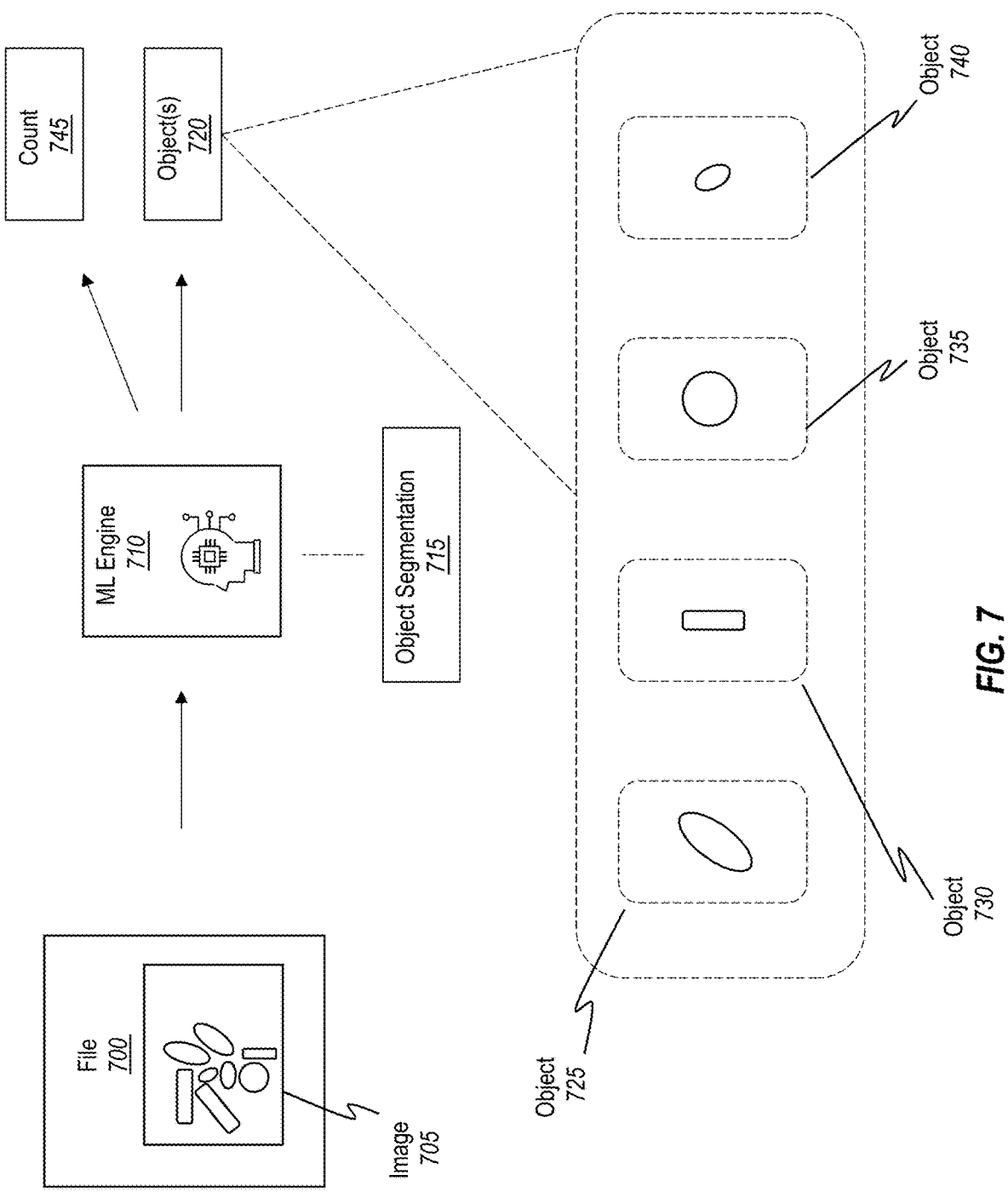
FIG. 7 illustrates how machine learning (ML) can be used to perform object segmentation in order to facilitate automatic counting and recognition of pills.

In some implementations, the server is able to harness machine learning (ML) to assist the medical professional in reviewing the imagery and other data provided by the client device. FIG. 7 is illustrative.

FIG. 7 shows a file 700, which is representative of the file 615 from FIG. 6. File 700 includes an image 705 of the user's pills.

The server computer system includes or has access to a ML engine 710 configured or trained to perform object segmentation 715. In this case, the ML engine 710 is trained to recognize and count pills. Optionally, the ML engine 710 is further trained to not only recognize pills but also to recognize which specific type a pill is. For example, the ML engine 710 can be trained to differentiate pill types based on size, color, shape, text on the pill, and so on.

Any type of ML algorithm, model, or machine learning may be used herein. As used herein, reference to "machine learning" or to a ML model may include any type of machine learning algorithm or device, neural network (e.g., convolutional neural network(s), multilayer neural network(s), recursive neural network(s), deep neural network(s), dynamic neural network(s), etc.), decision tree model(s) (e.g., decision trees, random forests, and gradient boosted trees), linear regression model(s) or logistic regression model(s), support vector machine(s) ("SVM"), artificial intelligence device(s), or any other type of intelligent computing system. Any amount of training data may be used (and perhaps later refined) to train the machine learning algorithm to dynamically perform the disclosed operations. Optionally, the ML engine 710 may be instantiated on the client device. In some cases, the ML engine 710 is instantiated in the cloud but is usable by the client device.

The ML engine 710 operates on the image 705 to segment and differentiate the different pill objects, as shown by object(s) 720. In this scenario, object(s) 720 include object 725, object 730, object 735, and object 740. Each of the objects 725-740 constitutes a different type of pill. Additionally, the ML engine 710 counts the number of pills, as shown by count 745.

By way of example, the ML engine 710 has recognized four different types of pills, including a large elliptical pill (object 725), a rectangular pill (object 730), a circular pill (object 735), and a small elliptical pill (object 740). That is, the ML engine 710 can perform object segmentation on an image to identify pills based on one or more of a shape, color, or size of the pills.

The ML engine 710 also recognizes the presence of 8 total pills in the image 705. The ML engine 710 is able to include the pill count 745 and the object(s) 720 in the database record that was generated earlier. The pill count 745 can be used as an auditable record.

Example Server-Side User Interfaces

Figure 15:
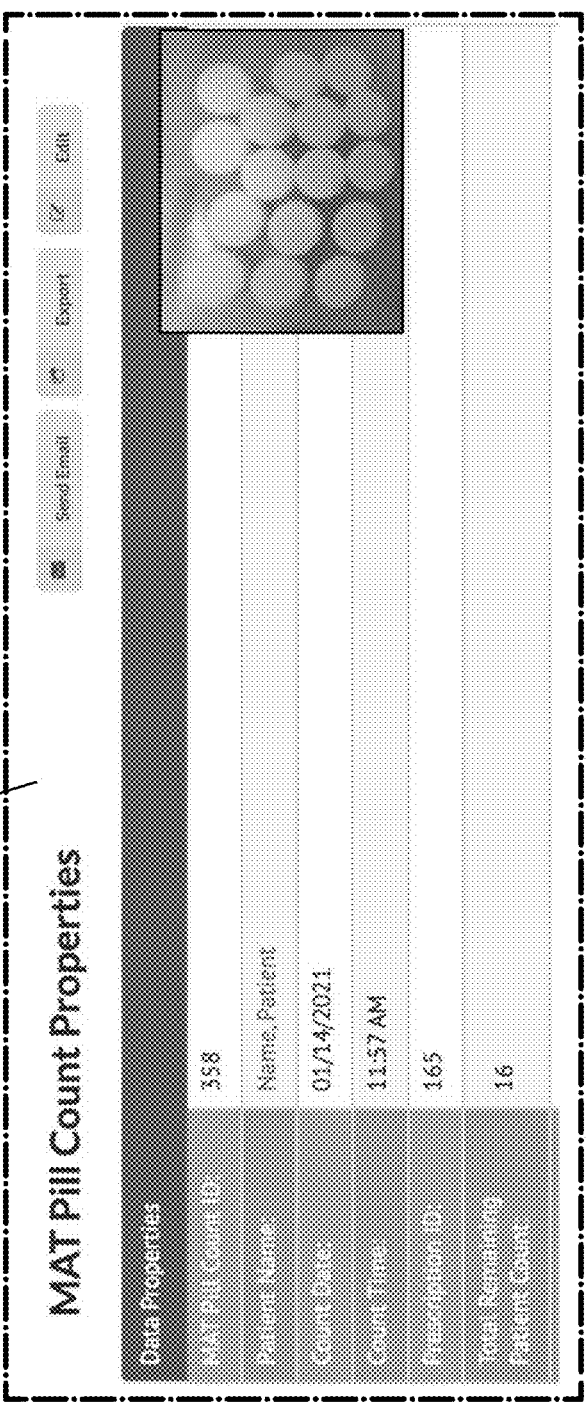
FIG. 15 illustrates an example UI showing various properties of a pill count record.
Figure 16:
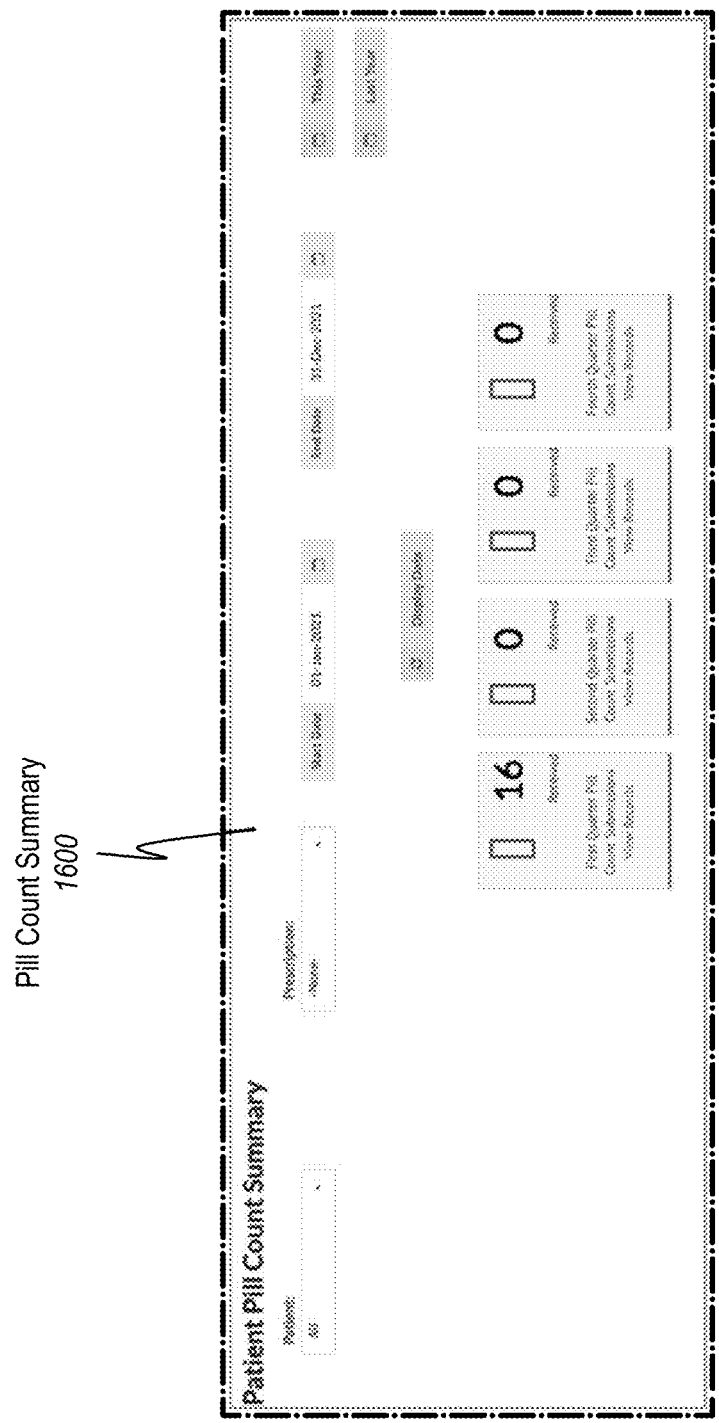
FIG. 16 illustrates a summary of a pill count event.
Figure 17:
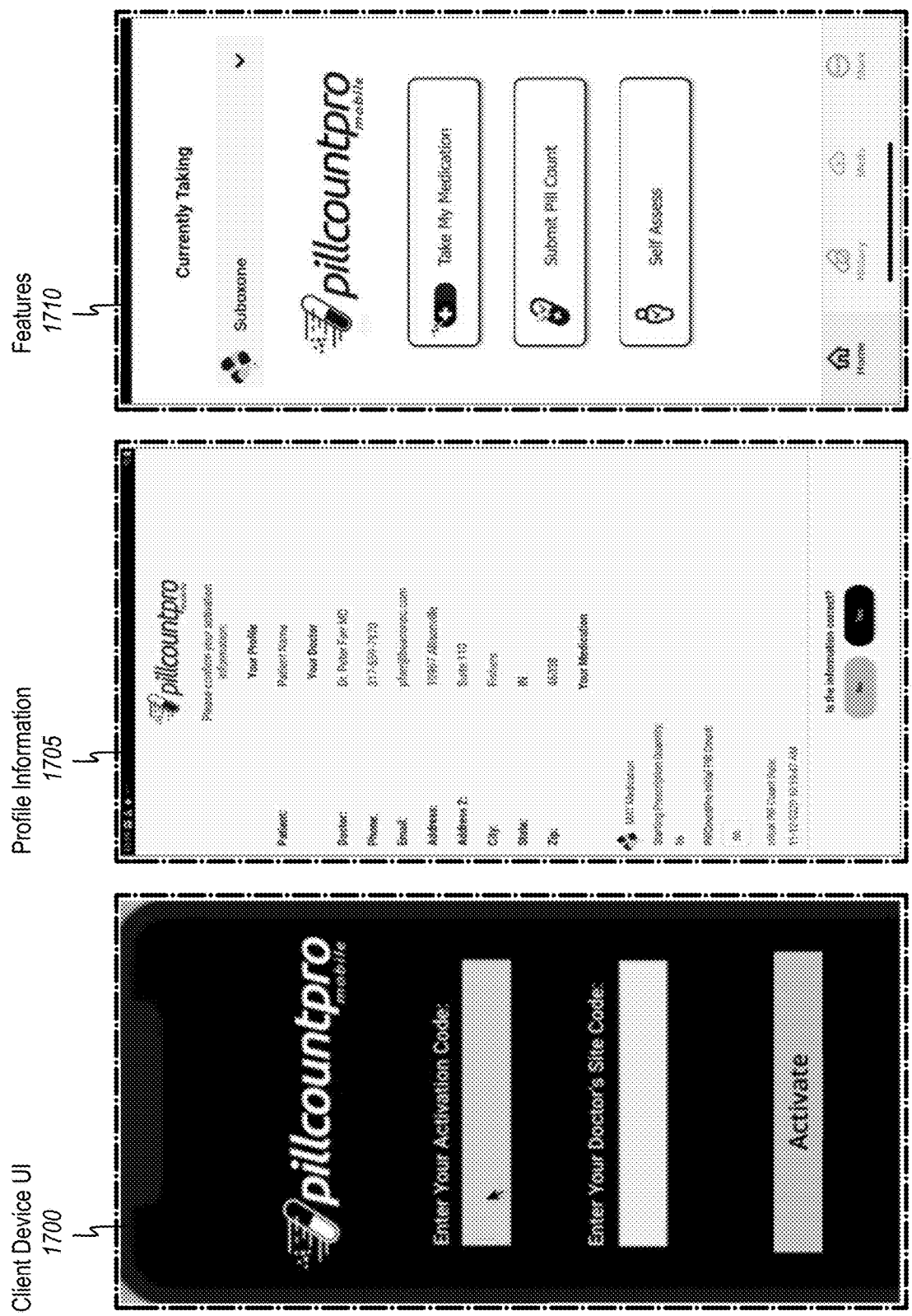
FIG. 17 illustrates various client-side example UIs.
Figure 18:
FIG. 18 illustrates a client-side dosage UI.
Figure 19:
FIG. 19 illustrates a client-side pill count UI.

Attention will now be directed to FIGS. 8 through 16, which illustrate various server-side user interfaces that may be presented to a medical professional accessing a patient's data on the server-end. FIGS. 17 through 19 illustrate various client-side user interfaces that may be presented to a patient on the client-end.

Figure 8:
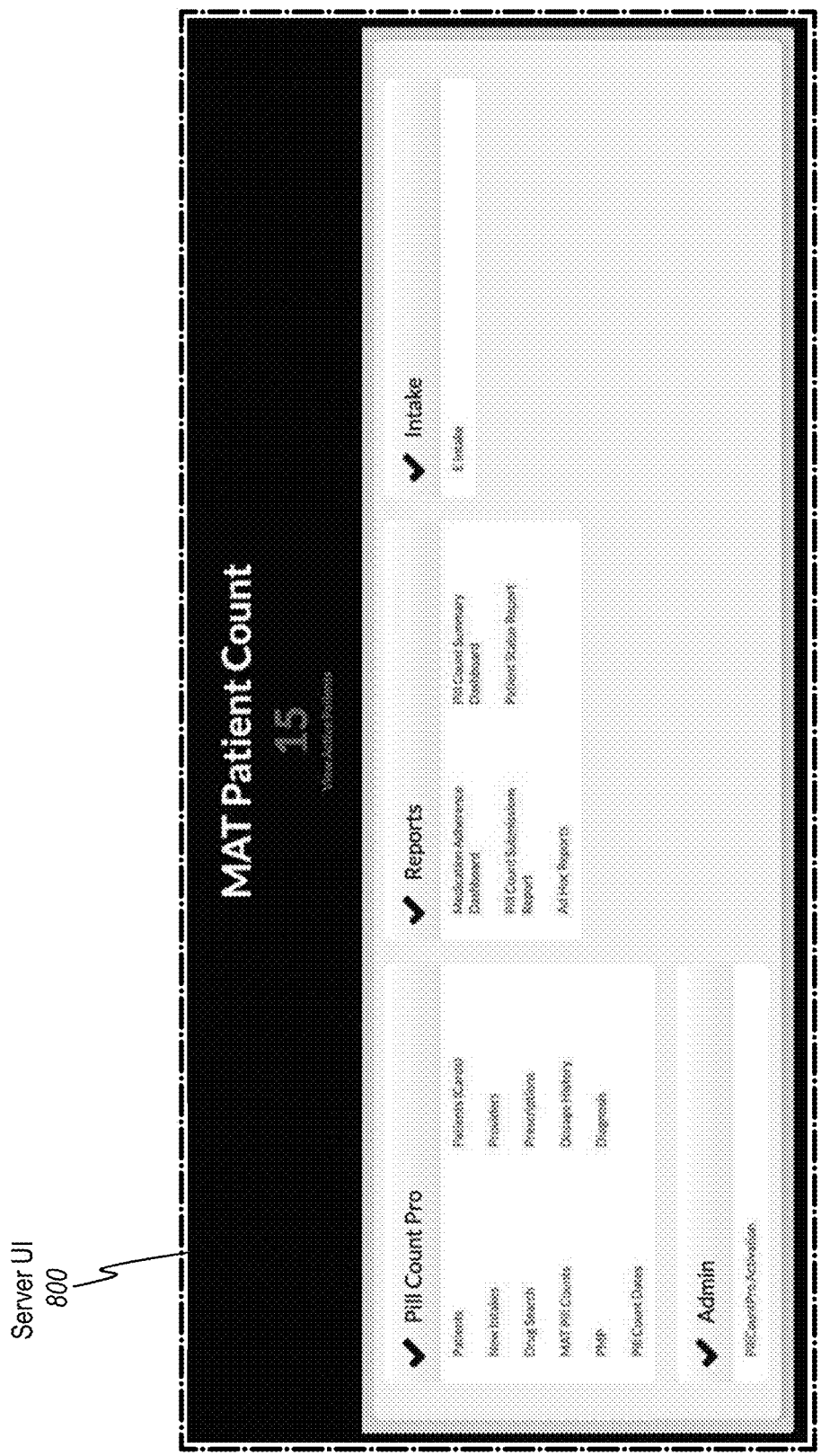
FIG. 8 illustrates a server-side user interface (UI) that is usable to track patients and patients' pill counts.
Figure 10:
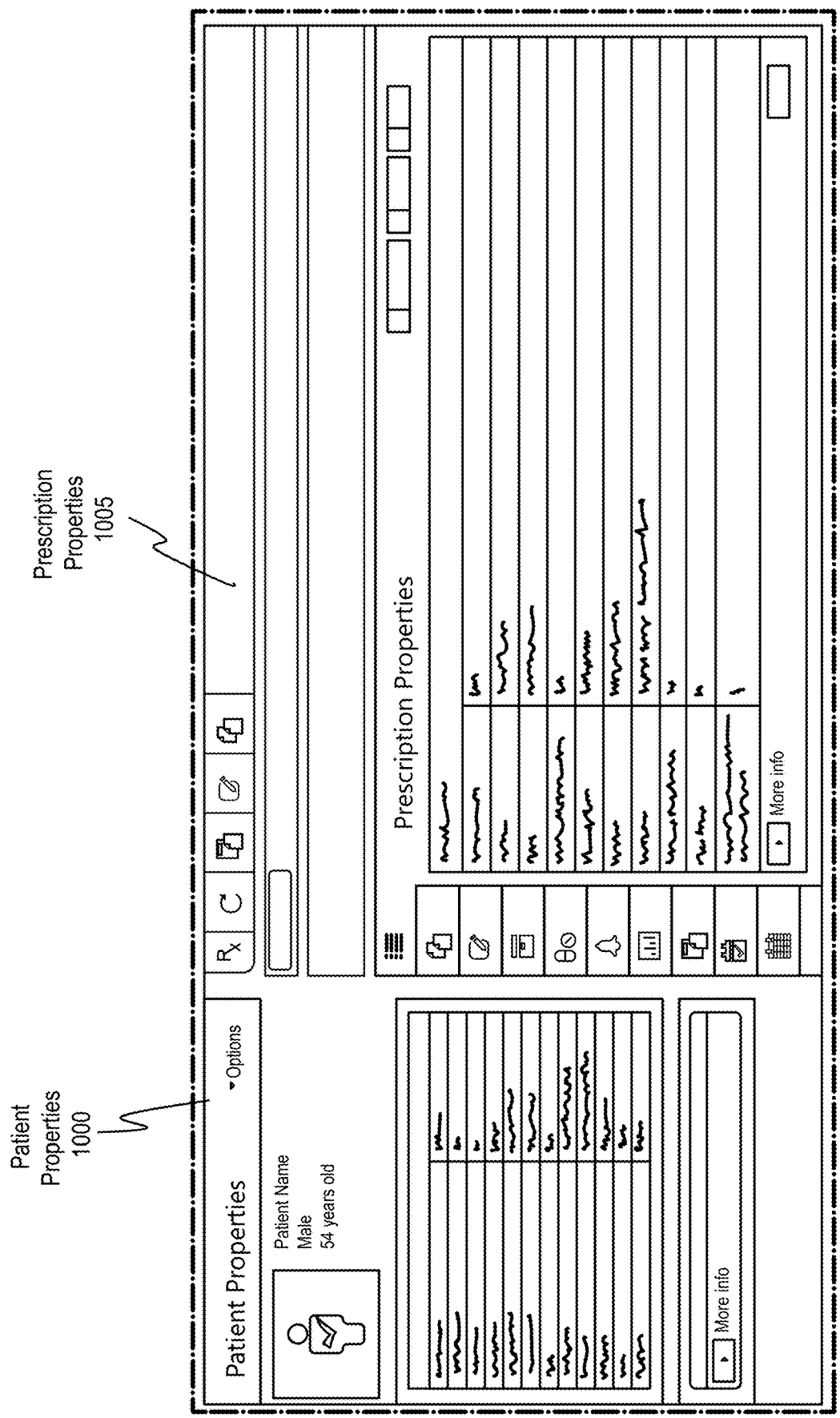
FIG. 10 illustrates an example UI structured to track properties of a patient and that patient's prescription details.

FIG. 8 shows an initial server UI 800, which operates as an initial dashboard for a user (e.g., a medical professional) accessing patient records from the server. Of course, the server-side application can be configured to require various levels of authentication in order to access the underlying data.

The dashboard or server UI 800 in FIG. 8 includes a number of options that are made available to the user. These options include, but are not limited to, options for verifying pill counts, options to generate reports, options for intaking new patients, and options for activating accounts.

FIG. 9 shows a provider properties 900 UI. This UI includes information that a user enters in order to activate or initiate an account. Some of the properties that are entered include whether the user is an "Authorized Medical Director." Other properties include DEA waiver limits, provider name, DEA number, address, and contact information.

Medical professionals treat patients. As such, the server-side application includes a UI structured to receive patient information, as shown by the patient properties 1000 UI in FIG. 10. The patient properties 1000 UI includes fields to enter a patient's name, date of birth, age, gender, and contact information.

The server-side application also includes a prescription properties 1005 UI, which enables a provider to enter information regarding which prescriptions a patient has for his/her medication assisted treatment. Such information may include the name of the drug, the dosage amounts or levels, the refill rate, and so on. Any information about a drug or about the patient's usage of that drug can be entered in the prescription properties 1005 UI. Such information is maintained in the server database mentioned earlier.

Figure 11:
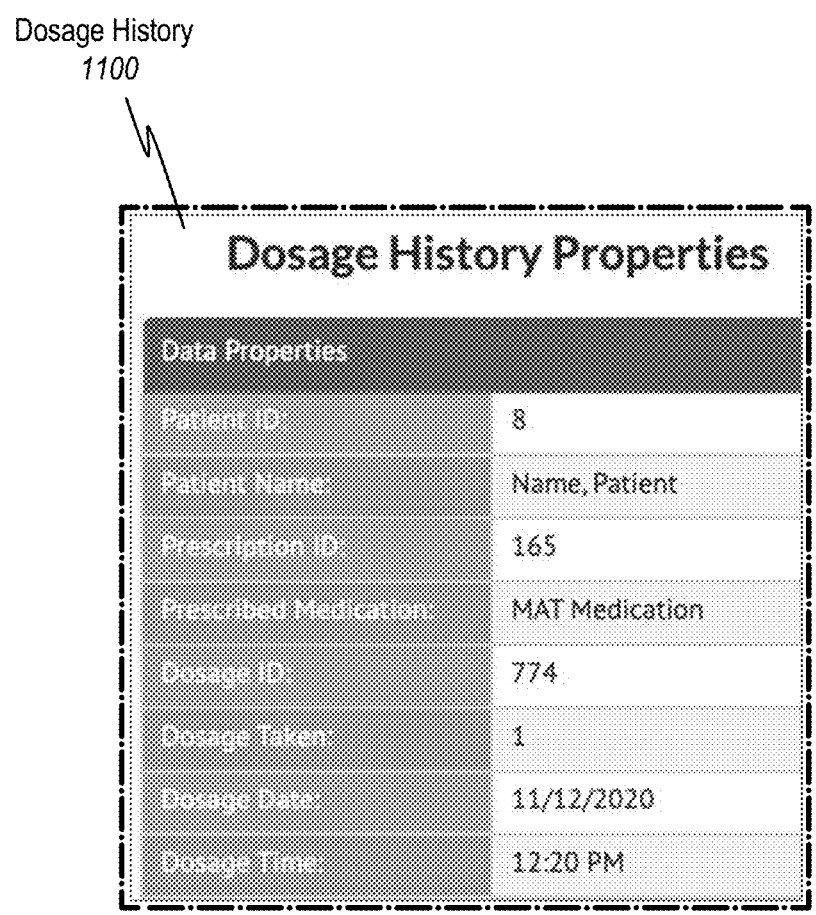
FIG. 11 illustrates an example UI structured to monitor dosage history.

Building on that understanding, the server-side application may include a dosage history 1100 UI, as shown in FIG. 11. This UI lists which dosage amounts a particular patient has for any given prescription. Additionally, the UI can list when a particular dosage was last taken and how much, as transmitted from the client device.

Figure 12:
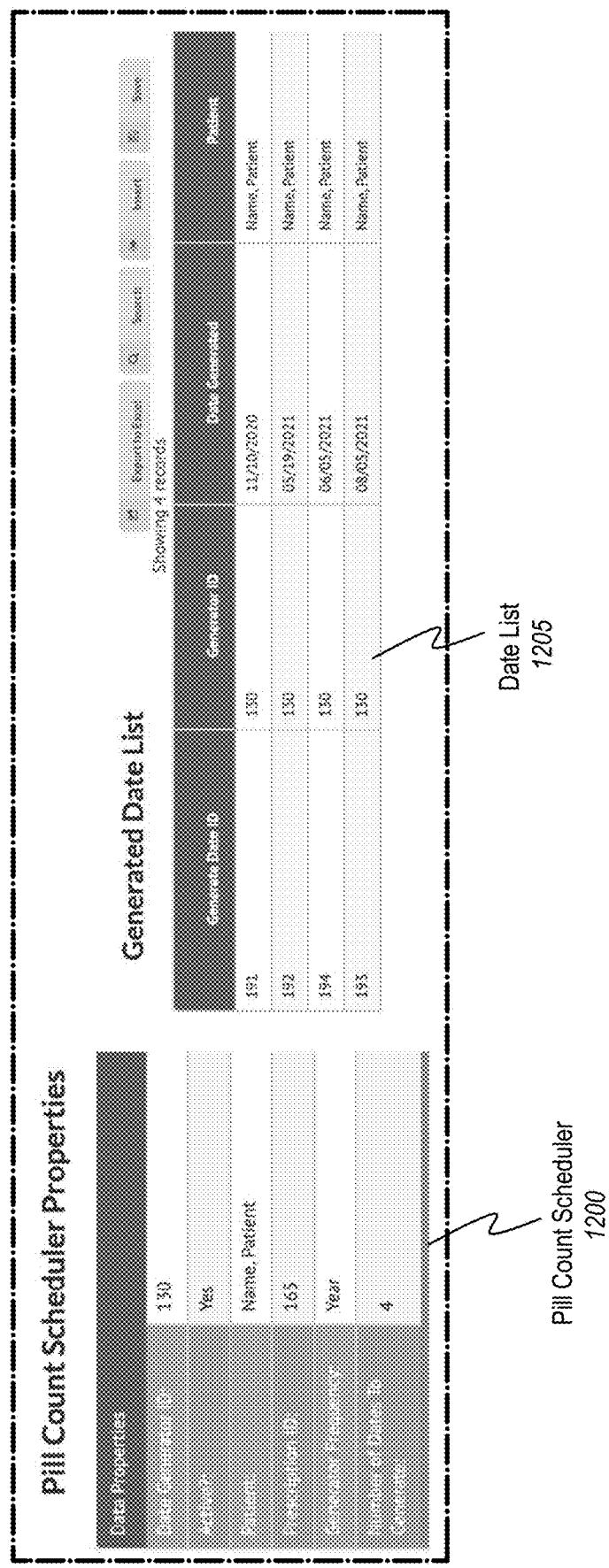
FIG. 12 illustrates an example UI structured to schedule and trigger pill count reminders.

FIG. 12 shows a pill count scheduler 1200 and a date list 1205. The pill count scheduler 1200 enables a medical professional to establish a frequency by which a patient is to submit a pill count to the medical professional. In FIG. 12, the pill count scheduler 1200 shows that for this scenario, the patient is to submit pill counts every quarter, or every three months (totaling four times a year). This scheduler is fully customizable and is used to trigger when reminder notifications (e.g., perhaps an SMS text message) will be sent to the patient.

The date list 1205 lists the specific dates (and potentially even times) when the pill count event was triggered and/or completed. That is, for each pill count event, there may be two log entries; one log entry providing a timestamp as to when the reminder or notification was initially transmitted and one log entry providing a timestamp as to when the pill count event information was finally received by the server. In some cases, a third log entry may be included, where the third entry lists the timestamp when the medical professional reviewed the pill count information. Yet another log entry may be provided in the event that additional follow-up is requested by the medical professional, such as in a case where the medical professional requests an additional pill count be conducted or other mitigation activities. Further details on such scenarios will be provided later.

Figure 13:
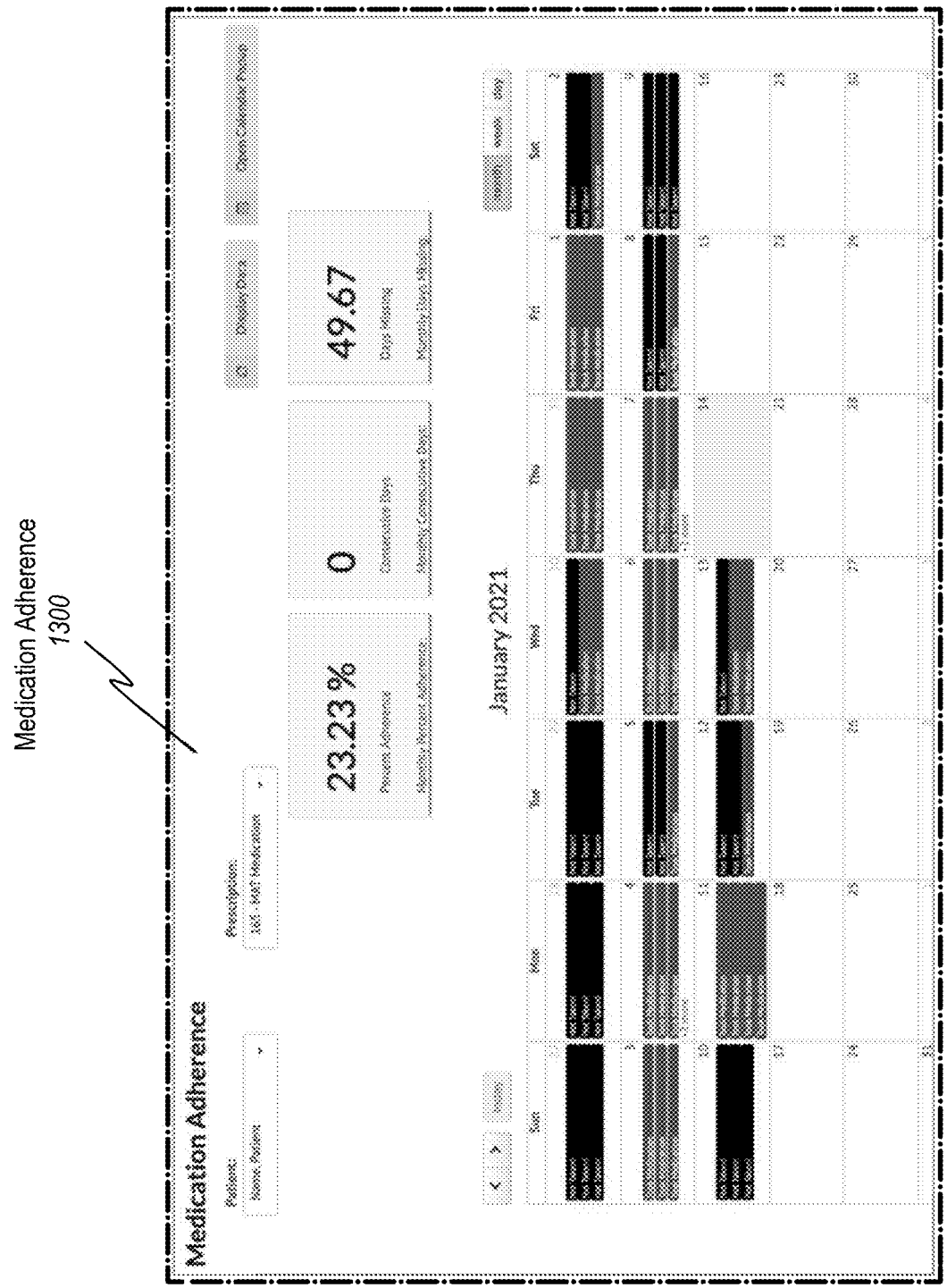
FIG. 13 illustrates an example UI structured to track adherence to a medication plan.
Figure 14:
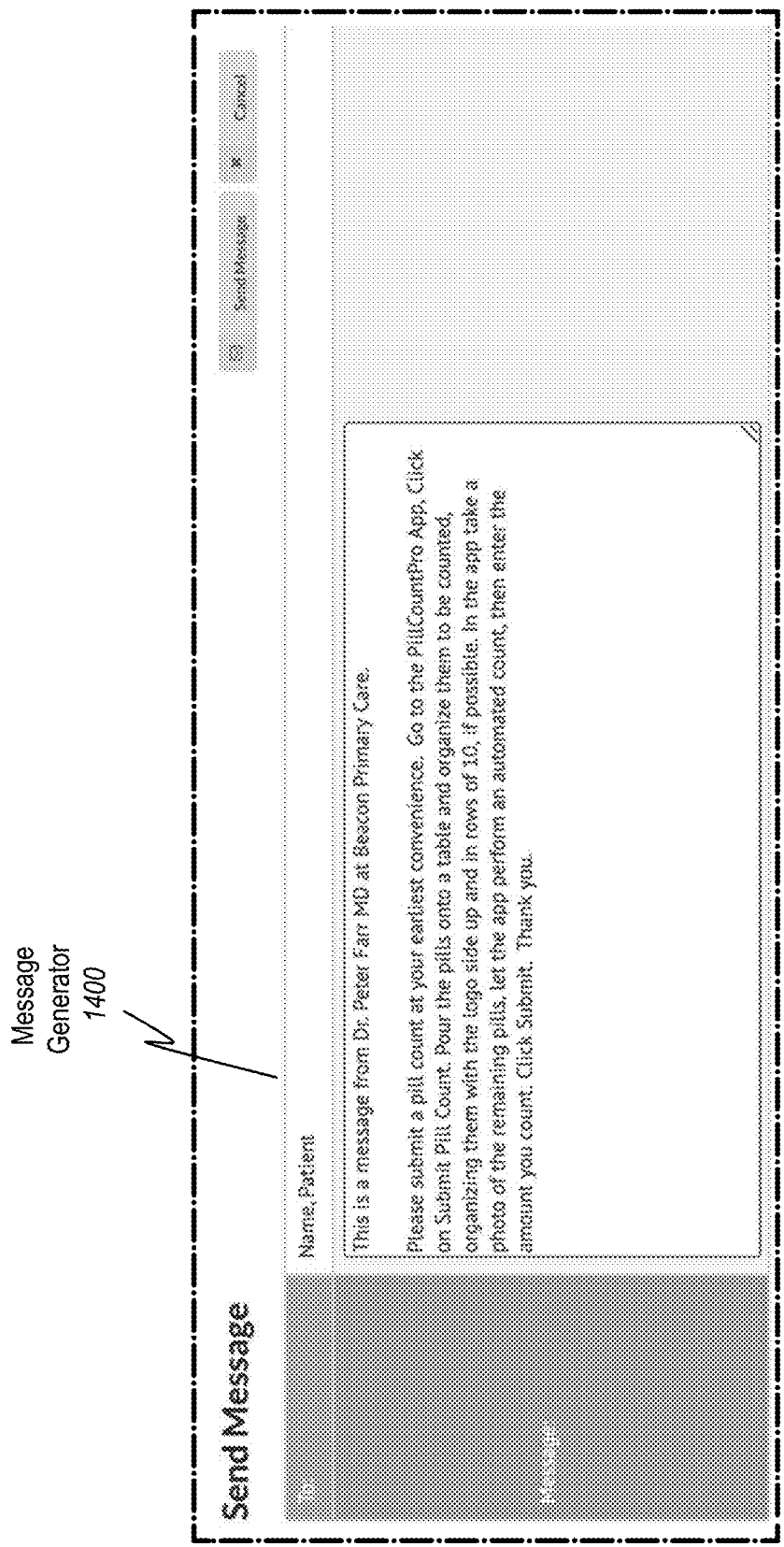
FIG. 14 illustrates an example UI structured to enable a health care provider to generate a reminder message for transmission to a patient.

FIG. 13 shows a medication adherence 1300 UI. In addition to counting pills, some embodiments additionally record or maintain logs as to when a patient takes or consumes his/her pills. The medication adherence 1300 UI lists which days a patient took his/her pills using one visual format (e.g., different shading or highlighting) and lists which days the patient neglected to take his/her pills using a different visual format. The medication adherence 1300 UI may include other information, such as the percentage of adherence (i.e. as a percentage, how often does the patient follow his/her schedule), a consecutive days counter (i.e. how many days in a row did the patient take the pills or did the patient miss taking the pills), and even a days missed indication (i.e. reflecting how many days the patient should have taken pills but did not). The medication adherence 1300 UI can include various filtering operations to filter views based on medicine type, patient name, and so on.

As discussed previously, the embodiments are able to transmit a message (e.g., perhaps an SMS message) to notify the patient that it is time to perform a pill count. The actual message that is delivered to the patient is fully customizable, as shown by the message generator 1400 of FIG. 14.

Optionally, the embodiments are able to automatically generate a default reminder message to instruct the patient to perform a pill count. Alternatively, a customized message may be provided. Such messages can be automatically generated and/or transmitted based on a determined schedule or reminder frequency, which can be determined, updated, or otherwise customized by the medical professional. That is, the embodiments are able to send a notification, which can be an automatically generated notification that is triggered for dissemination or transmission based on a determined frequency for performing a pill counting procedure.

FIG. 15 shows a pill count properties 1500 UI. This UI includes a thumbnail version of the image that the client device captured. Upon selecting the image, a full resolution version of the image can be displayed. The pill count properties 1500 UI also includes the patient's information, which is linked with the secret key mentioned earlier. The UI also includes additional metadata, such as when the pill count was conducted (e.g., a timestamp reflecting a time when the image was generated or when the pill counting procedure occurred, which timestamp can be included in metadata), the number of pills remaining, the types of pills observed, and so on. Some of the metadata is generated on the client side, such as the time, date, potentially the pill count, GPS data, and so on. Some of the metadata can be generated on the server side, such as the thumbnail image, results obtained from the ML engine performing object recognition on the image, and so on.

It is often beneficial to provide a quick summary dashboard or view of the patient's information. The pill count summary 1600 UI of FIG. 16 provides this quick view. In particular, the pill count summary 1600 UI provides a high level overview regarding the number of pills that were counted for each scheduled event.

In some cases, the summary view preemptively lists the number of pill counting events that are to occur in a given time period (e.g., perhaps four per year) and fills in the information when that information is eventually obtained. By way of example, the scenario shown in FIG. 16 shows four pill counting events, but only one of them has actually occurred (e.g., the first quarter showing 16 pills). In this scenario, the remaining three instances have not yet occurred, but the quick summary window still displays an indication for those events.

In some instances, the quick summary window (i.e. the pill count summary 1600 UI) shows information only for events that have already actually occurred. The window can refrain from showing data for events that have not yet occurred. After those events occur, the window is updated to reflect the new information.

Client-Side User Interfaces

The preceding discussion focused on various server-side user interfaces. FIGS. 17, 18, and 19 provide various client-side user interfaces. These UIs are displayed on the client devices mentioned earlier. Additionally, these UIs are designed in a manner to help OUD patients easily navigate the various fields.

FIG. 17 shows three separate user interfaces, including client device UI 1700, profile information 1705, and features 1710. The client device UI 1700 is an initial interface that may be provided to a patient in order to access or activate his/her account. Each patient may be provided with an activation code to initially establish an account. Each medical professional also has his/her own database instance, which is often referred to as a "site." The patient enters his/her activation code and the medical professional's site code, both of which may be received from the medical professional and/or from an activation wizard.

That is, in some cases, the patient initially enters his/her activation code and the site code. The activate button optionally calls a URL associated with the medical professional's database instance. The process of calling the URL can create the activation interface file from the server and can then download information into that patient's mobile app in order to access or activate an account. The loaded data includes: patient name, provider information (e.g., name/address/telephone number), and the prescription information (e.g., drug name/start date/daily doses/starting pill quantity).

The patient can then confirm his/her personal information in the profile information 1705 UI. This UI is able to receive the name, address, doctor, contact information, medication information, and so on of the patient. After confirming this information, the user/patient has an account with the medical professional's site or database.

The features 1710 UI enables the patient to perform a number of different operations. One operation involves tracking when the patient takes his/her medication, as shown by the selectable option entitled "Take My Medication." Another operation involves conducting and submitting a pill count, as shown by the selectable option entitled "Submit Pill Count." Another operation is a self-assessment, which helps the patient gauge his/her progress in how the medicine is administered and managed.

FIG. 18 shows a resulting window that may be displayed when the patient selects the "Take My Medication" option. Specifically, the dosage UI 1800 is displayed. This UI enables the patient to track when, where, and how he/she takes a pill. The UI also allows the patient to enter which specific pill he/she is taking along with the specific dosage (e.g., 1 pill, 1.25 pills, etc.). Selecting the "Take Dosage" option triggers the generation of a new record in the patient's log within the medical professional's database for medication adherence reports, as was discussed earlier.

FIG. 19 shows a resulting window that may be displayed when the patient selects the "Submit Pill Count" option. Specifically, the pill count UI 1900 is displayed. This UI enables the patient to track or count the number of pills he/she has remaining. Often, the patient navigates to this UI after receiving a notification from the database that a new pill count event is to occur.

The UI has a visual layout that includes a number of data entry fields. The placement and arrangement of these fields is designed to help the patient easily and intuitively conduct the pill count event.

Notice, the UI includes a field for selecting which medication is to be counted. In some instances, a specific type of medication is to be counted while in other instances all types of medications are to be counted at the same time. Optionally, the ML algorithm can identify, sort, differentiate, and count any number of different types of pills based on the provided image. The UI also includes a date and time field, which may be automatically populated. The date and time field can reflect the start date and time of the pill counting procedure, the end date and time of the pill counting procedure, a duration of the pill counting procedure, and/or a combination of any of the above.

The UI also includes an option for the patient to enter a manually counted number reflecting the number of pills the patient has. Alternatively, an automatically computed count of the number of pills may be determined based on a captured image.

Additionally, the UI includes an option for the patient to use the device's camera to snap a picture of the pills that are being counted. A thumbnail version or a full resolution version of the resulting image can be displayed in the pill count UI 1900. Notice, the image is displayed simultaneously and proximately to the pill count indicator and to the other fields mentioned above.

The pill count UI 1900 also includes a certification field. This field, when checked or otherwise selected, operates as a certification that the information provided by the patient is true and accurate. The certification is also displayed simultaneously and proximately to the image and to the pill count indicator.

These various pieces of information are then included in the "metadata" that was mentioned earlier. Additional data may also be included in the metadata, such as an image of the user, the GPS coordinates, the user's secret key, and so on.

After the certification has been checked, the pill count UI 1900 provides a "Submit" selectable option. When selected, this option or UI element triggers the generation and transmission of the data file mentioned earlier to be sent to the server, where the data file includes the user's secret key, the image, and the metadata. Notably, prior to transmission, the data file is encrypted using the various techniques mentioned earlier. Accordingly, the various client-side UIs described herein are designed to help facilitate the pill counting process. Such UIs are presented as having specific visual layouts designed to help the patient with the pill counting process.

Example Flow Processes

The following discussion now refers to a number of methods and method acts that may be performed. Although the method acts may be discussed in a certain order or illustrated in a flow chart as occurring in a particular order, no particular ordering is required unless specifically stated, or required because an act is dependent on another act being completed prior to the act being performed.

Figure 20:
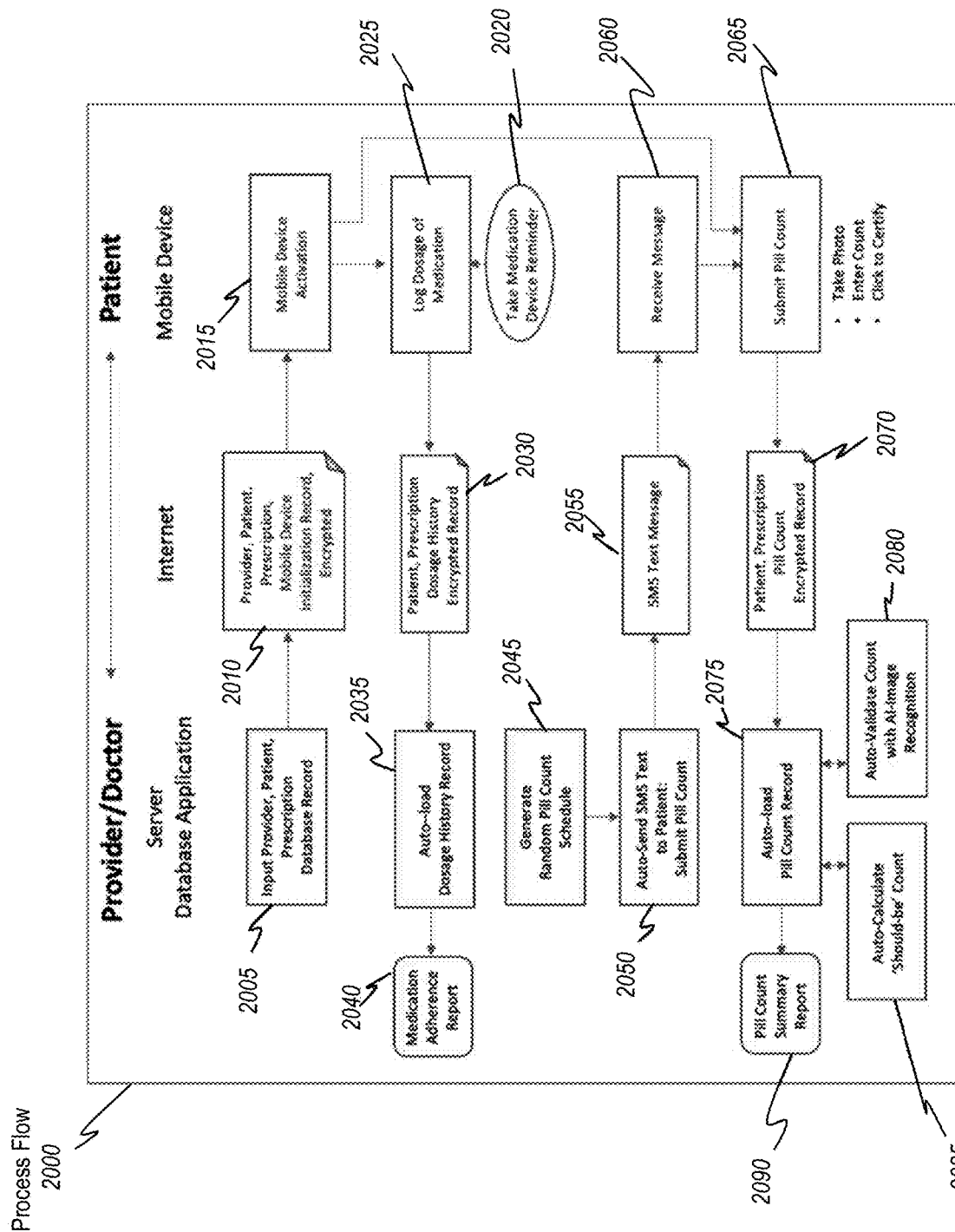
FIG. 20 illustrates an example flow chart for facilitating a pill counting procedure.

Attention will now be directed to FIG. 20, which illustrates a process flow 2000 that generally describes some of the operations involved with facilitating a pill count event. As shown in FIG. 20, the process flow 2000 involves two actors, or entities, namely: a "Server Database Application" and a "Mobile Device." The Server Database Application is representative of an application executing on the servers mentioned herein. Similarly, the Mobile Device is representative of the client devices mentioned herein. These two entities communicate over the Internet, a local area network, any other type of wide area network, and/or via a telecommunications network.

Initially, act 2005 involves compiling information from an input provider, such as a medical professional. This information includes the medical professional's information as well as potentially information about that professional's patients and the medications the patients are taking. In some cases, as shown in act 2010, the information is obtained over the Internet and is received from the client device (i.e. the mobile device).

In act 2015, a patient activates his/her account and establishes a set of one or more records within the medical professional's database instance. In act 2020, a reminder message, such as perhaps in the form of an SMS, is delivered to the mobile device to remind the patient to take his/her medication.

Act 2025 involves the patient logging a dosage of his/her medication. The dosage history or parameters are transmitted over the Internet, as shown by act 2030, where the server database application then logs or loads the dosage history into a new record for the patient (act 2035). Optionally, a medication adherence report can be generated for the medical professional to review and consider, as shown in act 2040.

When a new patient account is activated, the medical professional can use the server database application to generate a pill count schedule, as shown by act 2045. The schedule dictates or outlines the frequency by which the patient is to perform a pill count. When the scheduled time arrives for a patient's pill count, the server database application (as shown in act 2050) is able to automatically generate and automatically transmit a reminder message to the mobile device. Optionally, as shown by act 2055, the message may be in the form of an SMS message or email. Alternatively, the message may be transmitted over the Internet or even as a voice message. In act 2060, the mobile device receives the message and displays it in the form of a prompt for the patient to view.

In response to receiving the message, the patient is now informed that it is time to perform a pill count. The results of that pill count are later transmitted or submitted, as shown by act 2065. Those results are wrapped or contained in the data file mentioned earlier. In some instances, the data file is transmitted over the Internet, as shown by act 2070.

The server database application receives the data file and loads the information into its database, as shown by act 2075. In act 2080, the server database application validates the pill count metrics. Such validation can occur using ML to verify that the number entered by the patient is consistent with the number of pills identified using the ML algorithm executed against the image. In some cases, the final arbitration regarding the accuracy and authenticity is performed on the server-side.

In some implementations, the server database application, as shown in act 2085, executes the ML algorithm on the image and determines a pill count number. This auto-generated number is then be compared against the number provided by the client, as shown by act 2085. In act 2090, a pill count summary report is generated and may be provided to the medical professional.

Accordingly, some embodiments include a client computer system configured to surface (i.e. or "display") a user interface (UI) for facilitating a pill counting procedure. The system receives a notification from a server computer system, where the notification includes information instructing that a pill count is to be performed. In response to the notification, the system surfaces (i.e. "displays," or "renders") the UI to a user of the client computer system. This UI has a particular visual layout designed to facilitate the pill counting procedure. For example, the particular visual layout includes (1) a timestamp field indicating a date and time when the pill counting procedure is or was performed (e.g., a start time, end time, duration, or any of the above), (2) a pill count field indicating how many pills the user has, (3) an image field displaying an image of the pills the user has, (4) a certification field that, when selected, operates as a certification on the part of the user that the pill count is accurate, and (5) a submit field/button.

In response to the submit field being selected, the system generates an encrypted data file comprising (1) a secret key that de-identifies the user, (2) the image of the pills, and (3) metadata describing conditions associated with the pill count. The system then transmits the encrypted data file to the server computer system. In some cases, the notification that was previously received from the server computer system is transmitted via a different network than a network used to transmit the encrypted data file to the server computer system. For instance, the notification can be sent via a telecommunications network in the form of an SMS text message while the encrypted data file can be sent via the Internet or some other broadband network.

The server computer system is also configured to facilitate the pill counting procedure. For example, in response to a scheduled pill counting reminder being triggered, the server system transmits a notification to the client computer system. The notification includes information instructing a user of the client computer system to initiate a pill counting event.

Later, the server system receives, from the client computer system, an encrypted data file comprising (1) a secret key that de-identifies the user of the client computer system, (2) an image of pills the user has, and (3) metadata describing conditions associated with the pill counting event. The server system decrypts the encrypted data file to extract the secret key, the image, and the metadata. Based on the secret key, the server system identifies the user within a database managed by the server computer system and generates a new log record for the user within the database. The new log record comprises the image and the metadata. The server system also generates a report detailing the new log record. That report may be provided to a medical professional.

Mitigation Operations

In some implementations, various mitigation operations can be performed when suspicious data is received. For example, it may be the case that a discrepancy occurs between the pill count number determined by the ML algorithm and the pill count number that was provided by the patient. As another example, the ML algorithm can recognize and identify the various pills in the image and can determine that the pills in the image are not the pills that were originally prescribed to the patient (e.g., based on differences in size, color, shape, etc.).

As yet another example, the disclosed embodiments may determine suspicious activity is afoot if a large amount of time (i.e., a time surpassing a predefined threshold) elapses between the time when the initial reminder message is delivered to the patient and the time when the pill count is actually performed. Another suspicious activity may relate to the clarity of the image generated by the image (e.g., perhaps the lighting is too low or too high or perhaps the image resolution is too low or perhaps the angle is off). The embodiments are able to detect any number of activities and determine whether or not they amount to a suspicious activity.

Based on the determination that the received data is suspect, the embodiments are able to perform any number of mitigation operations in an attempt to resolve the suspiciousness. For example, suppose the quality of the received image is below a predetermined quality threshold. In such instances, the embodiments can automatically trigger a message to the patient instructing the patient to re-perform the pill count process. In some implementations, the message may include a statement that a higher quality image should be generated. In some implementations, the message may indicate which specific aspect of the image is deficient (e.g., the resolution is too low, the lighting is not adequate, etc.). This message can then be used to trigger a recount.

In some instances, the mitigation operations may involve notifying the medical professional. For example, when the computed pill count is different than the patient-provided pill count, the embodiments can transmit a message to a device owned by the medical professional to inform the professional of an apparent inconsistency. The professional can then review the materials to gauge how to respond. In some cases, the medical professional may determine that another pill count is warranted. In such situations, an option is provided to the professional to enable the professional to transmit a message to the patient informing the patient a re-do of the pill count is required. Accordingly, various different mitigation operations may be performed.

Audit Assurances

Via use of the disclosed architecture, the embodiments provide a robust platform that is easily auditable and that helps ensure compliance with government regulations. The platforms and UIs are easily scalable and customizable to account for changes in regulations.

Additionally, when an audit occurs, the medical professional can easily call up the database and show the auditing authorities all of the information that is needed for the audit. In this regard, the disclosed systems provide a robust and secure platform to help protect medical professionals and even patients when audits are performed.

Accordingly, implementations of the present invention include systems, methods, and computer program products that provide efficiency in the medical relationship, with particular regard to monitoring of end usage items, such as prescription medication.

For example, in some implementations, a client computer system configured to surface a user interface (UI) that facilitates a pill counting procedure can include one or more processors, and one or more computer-readable hardware storage devices that store instructions that are executable by the one or more processors. Upon execution, the instructions can cause the client computer system to at least receive a notification from a server computer system, where the notification includes information instructing that the pill counting procedure is to be performed. The system also surfaces (e.g., in response to the notification) the UI to a user of the client computer system, where the UI has a particular visual layout designed to facilitate the pill counting procedure. Optionally, the particular visual layout includes: (i) a timestamp field indicating a date and time when the pill counting procedure is performed; (ii) a pill count field indicating how many pills the user has remaining at that time; (iii) an image field displaying an image of the pills the user has; (iv) a certification field that, when selected, operates as a certification on a part of the user that the pill count is accurate; and (v) a submit field/button. The system can further be configured so that, in response to the submit field being selected, the system generates an encrypted data file comprising a secret key that de-identifies the user, a site code that identifies a database of a medical professional, the image of the pills, and metadata describing conditions associated with the pill count. The system can then transmit the encrypted data file to the server computer system.

In some embodiments, a server computer system is configured to facilitate a pill counting procedure. For instance, in response to a scheduled pill counting reminder being triggered, the server can transmit a notification to a client computer system. The notification includes information instructing a user of the client computer system to initiate a pill counting event. The server receives (e.g., from the client computer system) an encrypted data file comprising a secret key that de-identifies the user of the client computer system, a side code that identifies a database of a medical professional, an image of pills the user has, and metadata describing conditions associated with the pill counting event. The server then decrypts the encrypted data file to extract the secret key, the image, and the metadata. Based on the secret key, the server identifies the user within a database managed by the server computer system. The server also generates a new log record for the user within the database, where the new log record comprises the image and the metadata. Additionally, the server generates a report detailing the new log record.

Example Computer/Computer Systems

Figure 21:
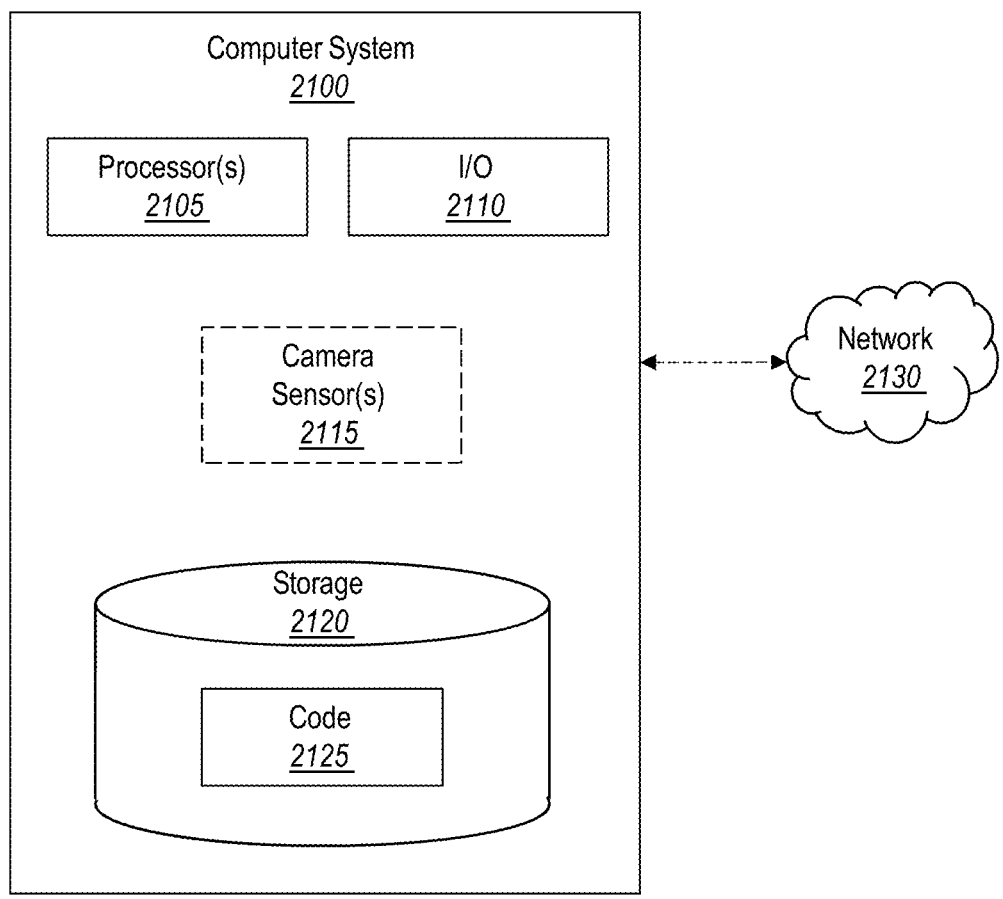
FIG. 21 illustrates an example computer system configured to perform any of the disclosed operations.

Attention will now be directed to FIG. 21 which illustrates an example computer system 2100 that may include and/or be used to perform any of the operations described herein. Computer system 2100 may take various different forms. For example, computer system 2100 may be embodied as a tablet, a desktop, a laptop, a mobile device, or a standalone device, a server, a client device, a wearable device, or any other type of computing system. Computer system 2100 may also be a distributed system that includes one or more connected computing components/devices that are in communication with computer system 2100.

In its most basic configuration, computer system 2100 includes various different components. FIG. 21 shows that computer system 2100 includes one or more processor(s) 2105 (aka a "hardware processing unit"), input/output 2110, one or more camera(s) 2115, and storage 2120. The one or more camera(s) 2115 are illustrated using a dotted box because it may be the case that not all computing systems have a camera.

Regarding the processor(s) 2105, it will be appreciated that the functionality described herein can be performed, at least in part, by one or more hardware logic components (e.g., the processor(s) 2105). For example, and without limitation, illustrative types of hardware logic components/processors that can be used include Field-Programmable Gate Arrays ("FPGA"), Program-Specific or Application-Specific Integrated Circuits ("ASIC"), Program-Specific Standard Products ("ASSP"), System-On-A-Chip Systems ("SOC"), Complex Programmable Logic Devices ("CPLD"), Central Processing Units ("CPU"), Graphical Processing Units ("GPU"), or any other type of programmable hardware.

I/O 2110 includes any type of input or output device. Examples of such devices include, but are not limited to, any type of touchscreen, keyboard, mouse, speaker, microphone, and so forth.

Camera(s) 2115 can include any type of camera. For instance, camera(s) 2115 can include any type of visible light camera or monochrome camera.

As used herein, the terms "executable module," "executable component," "component," "module," or "engine" can refer to hardware processing units or to software objects, routines, or methods that may be executed on computer system 2100. The different components, modules, engines, and services described herein may be implemented as objects or processors that execute on computer system 2100 (e.g. as separate threads).

Storage 2120 may be physical system memory, which may be volatile, non-volatile, or some combination of the two. The term "memory" may also be used herein to refer to non-volatile mass storage such as physical storage media. If computer system 2100 is distributed, the processing, memory, and/or storage capability may be distributed as well.

Storage 2120 is shown as including executable instructions (i.e. code 2125). The executable instructions represent instructions that are executable by the processor(s) 2105 (or perhaps even the ML engine) of computer system 2100 to perform the disclosed operations, such as those described in the various methods.

The disclosed embodiments may comprise or utilize a special-purpose or general-purpose computer including computer hardware, such as, for example, one or more processors (such as processor(s) 2105) and system memory (such as storage 2120), as discussed in greater detail below. Embodiments also include physical and other computer-readable media for carrying or storing computer-executable instructions and/or data structures. Such computer-readable media can be any available media that can be accessed by a general-purpose or special-purpose computer system. Computer-readable media that store computer-executable instructions in the form of data are "physical computer storage media" or a "hardware storage device." Computer-readable media that carry computer-executable instructions are "transmission media." Thus, by way of example and not limitation, the current embodiments can comprise at least two distinctly different kinds of computer-readable media: computer storage media and transmission media.

Computer storage media (aka "hardware storage device") are computer-readable hardware storage devices, such as RAM, ROM, EEPROM, CD-ROM, solid state drives ("SSD") that are based on RAM, Flash memory, phase-change memory ("PCM"), or other types of memory, or other optical disk storage, magnetic disk storage or other magnetic storage devices, or any other medium that can be used to store desired program code means in the form of computer-executable instructions, data, or data structures and that can be accessed by a general-purpose or special-purpose computer.

Computer system 2100 may also be connected (via a wired or wireless connection) to external sensors (e.g., one or more remote cameras) or devices via a network 2130. For example, computer system 2100 can communicate with any number devices, servers, or cloud services to obtain or process data. In some cases, network 2130 may itself be a cloud network. Furthermore, computer system 2100 may also be connected through one or more wired or wireless networks 2130 to remote/separate computer systems(s) that are configured to perform any of the processing described with regard to computer system 2100.

A "network," like network 2130, is defined as one or more data links and/or data switches that enable the transport of electronic data between computer systems, modules, and/or other electronic devices. When information is transferred, or provided, over a network (either hardwired, wireless, or a combination of hardwired and wireless) to a computer, the computer properly views the connection as a transmission medium. Computer system 2100 will include one or more communication channels that are used to communicate with the network 2130. Transmissions media include a network that can be used to carry data or desired program code means in the form of computer-executable instructions or in the form of data structures. Further, these computer-executable instructions can be accessed by a general-purpose or special-purpose computer. Combinations of the above should also be included within the scope of computer-readable media.

Upon reaching various computer system components, program code means in the form of computer-executable instructions or data structures can be transferred automatically from transmission media to computer storage media (or vice versa). For example, computer-executable instructions or data structures received over a network or data link can be buffered in RAM within a network interface module (e.g., a network interface card or "NIC") and then eventually transferred to computer system RAM and/or to less volatile computer storage media at a computer system. Thus, it should be understood that computer storage media can be included in computer system components that also (or even primarily) utilize transmission media.

Computer-executable (or computer-interpretable) instructions comprise, for example, instructions that cause a general-purpose computer, special-purpose computer, or special-purpose processing device to perform a certain function or group of functions. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the embodiments may be practiced in network computing environments with many types of computer system configurations, including personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, and the like. The embodiments may also be practiced in distributed system environments where local and remote computer systems that are linked (either by hardwired data links, wireless data links, or by a combination of hardwired and wireless data links) through a network each perform tasks (e.g. cloud computing, cloud services and the like). In a distributed system environment, program modules may be located in both local and remote memory storage devices.

The present invention may be embodied in other specific forms without departing from its characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A client computer system configured to surface a user interface (UI) for facilitating a pill counting procedure, said client computer system comprising:
one or more processors; and
one or more computer-readable hardware storage devices that store instructions that are executable by the one or more processors to cause the client computer system to at least:
receive a notification from a server computer system, wherein the notification includes information instructing that the pill counting procedure is to be performed;
in response to the notification, surface the user interface (UI) to a user of the client computer system, the UI having a particular visual layout designed to facilitate the pill counting procedure, wherein the particular visual layout includes:
a timestamp field indicating a date and time when the pill counting procedure is performed;
a pill count field indicating how many pills the user has;
an image field displaying an image of the pills the user has, wherein said image is included as a part of a composite image that is generated by a back-facing camera of the client computer system, wherein a front-facing camera of the client computer system generates a second image of the user while the back-facing camera generates the image, and wherein the composite image includes both the image and the second image such that a likeness of both the user and the pills are displayed in the same composite image;
a certification field that, when selected, operates as a certification on a part of the user that the pill count is accurate; and
a submit field;
in response to the submit field being selected, generate an encrypted data file comprising a secret key that de-identifies the user, a site code that identifies a database of a medical professional, the image of the pills, and metadata describing conditions associated with the pill count; and
transmit the encrypted data file to the server computer system.

2. The client computer system of claim 1, wherein the image of the pills is embedded with the date and time when the pill counting procedure was performed.

3. The client computer system of claim 1, wherein the notification received from the server computer system is received via a short message service (SMS) text message.

4. The client computer system of claim 3, wherein the encrypted data file is transmitted to the server computer system using an internet protocol (IP) protocol.

5. The client computer system of claim 1, wherein the notification received from the server computer system is transmitted via a different network than a network used to transmit the encrypted data file to the server computer system.

6. The client computer system of claim 1, wherein a machine learning algorithm performs object segmentation on the image of the pills to count the pills.

7. The client computer system of claim 1, wherein a machine learning algorithm performs object segmentation on the image to determine a type for each pill represented within the image.

8. The client computer system of claim 1, wherein the encrypted data file is directed to a uniform resource locator (URL) associated with the server computer system, and wherein an application programming interface (API) intercepts the encrypted data file.

9. The client computer system of claim 1, wherein the metadata includes a fingerprint of the user.

10. A method for surfacing a user interface (UI) configured to facilitate a pill counting procedure, said method being performed by a client computer system and comprising:
receiving a notification from a server computer system, wherein the notification includes information instructing that the pill counting procedure is to be performed;
in response to the notification, surfacing the user interface (UI) to a user of the client computer system, the UI having a particular visual layout designed to facilitate the pill counting procedure, wherein the particular visual layout includes:
a timestamp field indicating a date and time when the pill counting procedure is performed;
a pill count field indicating how many pills the user has;
an image field displaying an image of the pills the user has, wherein said image is included as a part of a composite image that is generated by a back-facing camera of the client computer system, wherein a front-facing camera of the client computer system generates a second image of the user while the back-facing camera generates the image, and wherein the composite image includes both the image and the second image such that a likeness of both the user and the pills are displayed in the same composite image;
a certification field that, when selected, operates as a certification on a part of the user that the pill count is accurate; and
a submit field;
in response to the submit field being selected, generating an encrypted data file comprising a secret key that de-identifies the user, a site code that identifies a database of a medical professional, the image of the pills, and metadata describing conditions associated with the pill count; and
transmitting the encrypted data file to the server computer system.

11. The method of claim 10, wherein the metadata further includes a time counter reflecting an amount of time that elapsed from a time when the notification was received to a time when the encrypted data file was transmitted.

12. The method of claim 10, wherein the metadata includes a voice recording of the user, the voice recording operating as verification of an identity of the user.

13. The method of claim 10, wherein the metadata includes global positioning system (GPS) location data indicating a location where the image was generated.

14. The method of claim 10, wherein the encrypted data file is encrypted using a secure hash algorithm-1 (SHA-1) cryptographic has function.

15. The method of claim 10, wherein a machine learning algorithm performs object segmentation on the image to identify pills based on one or more of a shape of the pills, color of the pills, text on the pills, or size of the pills.

16. The method of claim 10, wherein the notification is an automatically generated notification that is triggered for dissemination based on a determined frequency for performing the pill counting procedure.

17. A server computer system configured to facilitate a pill counting procedure, said server computer system comprising:
one or more processors; and one or more computer-readable hardware storage devices that store instructions that are executable by the one or more processors to cause the server computer system to at least:

in response to a scheduled pill counting reminder being triggered, transmit a notification to a client computer system, the notification including information instructing a user of the client computer system to initiate a pill counting event;

receive, from the client computer system, an encrypted data file comprising a secret key that de-identifies the user of the client computer system, a side code that identifies a database of a medical professional, an image of pills the user has, and metadata describing conditions associated with the pill counting event, wherein said image is included as a part of a composite image that is generated by a back-facing camera of the client computer system, wherein a front-facing camera of the client computer system generates a second image of the user while the back-facing camera generates the image, and wherein the composite image includes both the image and the second image such that a likeness of both the user and the pills are displayed in the same composite image;

decrypt the encrypted data file to extract the secret key, the image, and the metadata;

based on the secret key, identify the user within a database managed by the server computer system;

generate a new log record for the user within the database, the new log record comprising the image and the metadata; and generate a report detailing the new log record.

18. The server computer system of claim 17, wherein the metadata includes global positioning system (GPS) location reflecting a location where the image was generated.

19. The server computer system of claim 17, wherein the metadata includes a timestamp reflecting a time when the image was generated.

20. The server computer system of claim 17, wherein the image of the pills is embedded with the date and time when the pill counting procedure was performed, and wherein a machine learning algorithm performs object segmentation on the image of the pills to count the pills.

* * * * *